US008231683B2

(12) United States Patent
Lappin et al.

(10) Patent No.: US 8,231,683 B2
(45) Date of Patent: Jul. 31, 2012

(54) SHOULDER PROSTHESIS ASSEMBLY HAVING GLENOID RIM REPLACEMENT STRUCTURE

(75) Inventors: Kyle Lappin, Fort Wayne, IN (US); Matt Stone, Warsaw, IN (US); Lieven De Wilde, Ghent (BE); Joseph Iannotti, Strongsville, OH (US); Carl Basamania, Seattle, WA (US)

(73) Assignee: DePuy Products, Inc., Warsaw, IN (US)

( * ) Notice: Subject to any disclaimer, the term of this patent is extended or adjusted under 35 U.S.C. 154(b) by 132 days.

(21) Appl. No.: 12/632,865

(22) Filed: Dec. 8, 2009

(65) Prior Publication Data

US 2011/0137424 A1 Jun. 9, 2011

(51) Int. Cl.
*A61F 2/40* (2006.01)
(52) U.S. Cl. .................................. 623/19.11
(58) Field of Classification Search .... 623/19.11–19.14, 623/20.32; *A61F 2/40*
See application file for complete search history.

(56) References Cited

U.S. PATENT DOCUMENTS

| | | |
|---|---|---|
| 3,061,977 A | 11/1962 | Schmidt |
| 3,694,820 A | 10/1972 | Scales et al. |
| 3,837,008 A | 9/1974 | Bahler et al. |
| 3,855,638 A | 12/1974 | Piliar |
| 4,040,130 A | 8/1977 | Laure |
| 4,042,980 A | 8/1977 | Swanson et al. |
| 4,045,825 A | 9/1977 | Stroot |
| 4,045,826 A | 9/1977 | Stroot |
| 4,106,128 A | 8/1978 | Greenwald et al. |
| 4,172,296 A | 10/1979 | D'Errico |
| 4,180,871 A | 1/1980 | Hamas |
| 4,524,467 A | 6/1985 | DeCarlo, Jr. |
| 4,550,450 A | 11/1985 | Kinnett |
| D285,968 S | 9/1986 | Kinnett |
| 4,693,723 A | 9/1987 | Gabard |
| 4,695,282 A | 9/1987 | Forte et al. |

(Continued)

FOREIGN PATENT DOCUMENTS

DE 102006041550 A1 11/2007

(Continued)

OTHER PUBLICATIONS

EPO Search Report for EPO App. No. 07253676.6-2310 Dated Jan. 8, 2008.

(Continued)

*Primary Examiner* — Thomas J Sweet
*Assistant Examiner* — Jason-Dennis Stewart
(74) *Attorney, Agent, or Firm* — Maginot, Moore & Beck, LLP

(57) ABSTRACT

A prosthesis assembly for use with a scapula is disclosed. The prosthesis assembly includes a glenoid bearing support and a bearing. The glenoid bearing support includes a glenoid vault-occupying portion configured to occupy at least a portion of a glenoid vault of the scapula, the glenoid-vault occupying portion having a first coupling component. The glenoid bearing support further includes a glenoid rim replacement portion attached to the glenoid vault-occupying portion. The bearing defines a bearing surface and has a second coupling component configured to cooperate with the first coupling component to couple the bearing to the glenoid vault-occupying portion. The glenoid vault-occupying portion defines a bearing-side end portion and an opposite-side end portion. The glenoid rim replacement portion projects outwardly from the bearing-side end portion of the glenoid vault-occupying portion. The glenoid bearing support defines a bone graft receptacle.

16 Claims, 19 Drawing Sheets

U.S. PATENT DOCUMENTS

| | | |
|---|---|---|
| 4,795,468 A | 1/1989 | Hodorek et al. |
| 4,865,025 A | 9/1989 | Buzzi et al. |
| 4,865,605 A | 9/1989 | Dines et al. |
| 4,919,670 A | 4/1990 | Dale et al. |
| 4,936,853 A | 6/1990 | Fabian et al. |
| 4,964,865 A | 10/1990 | Burkhead et al. |
| 4,986,833 A | 1/1991 | Worland |
| 4,987,904 A | 1/1991 | Wilson |
| 5,030,219 A | 7/1991 | Matsen, III et al. |
| 5,032,132 A | 7/1991 | Matsen, III et al. |
| 5,047,058 A | 9/1991 | Roberts et al. |
| 5,080,673 A | 1/1992 | Burkhead et al. |
| 5,108,446 A | 4/1992 | Wagner et al. |
| 5,150,304 A | 9/1992 | Berchem et al. |
| 5,197,465 A | 3/1993 | Montgomery |
| 5,201,882 A | 4/1993 | Paxson |
| 5,304,181 A | 4/1994 | Caspari et al. |
| 5,314,479 A | 5/1994 | Rockwood, Jr. et al. |
| 5,344,461 A | 9/1994 | Phlipot |
| 5,358,526 A | 10/1994 | Tornier |
| 5,370,693 A | 12/1994 | Kelman et al. |
| 5,387,241 A | 2/1995 | Hayes |
| 5,437,677 A | 8/1995 | Shearer et al. |
| 5,458,637 A | 10/1995 | Hayes |
| 5,474,559 A | 12/1995 | Bertin et al. |
| 5,486,180 A | 1/1996 | Dietz et al. |
| 5,489,309 A | 2/1996 | Lackey et al. |
| 5,489,310 A | 2/1996 | Mikhail |
| 5,496,324 A | 3/1996 | Barnes |
| 5,507,821 A | 4/1996 | Sennwald et al. |
| 5,554,158 A | 9/1996 | Vinciguerra et al. |
| 5,593,441 A | 1/1997 | Lichtenstein et al. |
| 5,593,448 A | 1/1997 | Dong |
| 5,601,563 A | 2/1997 | Burke et al. |
| 5,665,090 A | 9/1997 | Rockwood et al. |
| 5,702,447 A | 12/1997 | Walch et al. |
| 5,718,360 A | 2/1998 | Green et al. |
| 5,723,018 A | 3/1998 | Cyprien et al. |
| 5,743,915 A | 4/1998 | Bertin et al. |
| 5,769,855 A | 6/1998 | Bertin et al. |
| 5,779,710 A | 7/1998 | Matsen, III |
| 5,782,924 A | 7/1998 | Johnson |
| 5,800,551 A | 9/1998 | Williamson et al. |
| 5,853,415 A | 12/1998 | Bertin et al. |
| 5,860,981 A | 1/1999 | Bertin et al. |
| 5,879,401 A | 3/1999 | Besemer et al. |
| 5,908,424 A | 6/1999 | Bertin et al. |
| 5,928,285 A | 7/1999 | Bigliani et al. |
| 5,976,145 A | 11/1999 | Kennefick, III |
| 6,045,582 A | 4/2000 | Prybyla |
| 6,096,084 A | 8/2000 | Townley |
| 6,139,581 A | 10/2000 | Engh et al. |
| 6,197,062 B1 | 3/2001 | Fenlin |
| 6,197,063 B1 | 3/2001 | Dews |
| 6,206,925 B1 | 3/2001 | Tornier |
| 6,228,119 B1 | 5/2001 | Ondrla et al. |
| 6,228,900 B1 | 5/2001 | Shen et al. |
| 6,245,074 B1 | 6/2001 | Allard et al. |
| 6,281,264 B1 | 8/2001 | Salovey et al. |
| 6,364,910 B1 | 4/2002 | Shultz et al. |
| 6,368,353 B1 | 4/2002 | Arcand |
| 6,379,386 B1 | 4/2002 | Resch et al. |
| 6,398,812 B1 | 6/2002 | Masini |
| 6,406,495 B1 | 6/2002 | Schoch |
| 6,488,715 B1 | 12/2002 | Pope et al. |
| 6,514,287 B2 | 2/2003 | Ondrla et al. |
| 6,620,197 B2 | 9/2003 | Maroney et al. |
| 6,673,115 B2 | 1/2004 | Resch et al. |
| 6,676,705 B1 | 1/2004 | Wolf |
| 6,679,916 B1 | 1/2004 | Frankle et al. |
| 6,699,289 B2 | 3/2004 | Iannotti et al. |
| 6,780,190 B2 | 8/2004 | Maroney |
| 6,783,549 B1 | 8/2004 | Stone et al. |
| 6,821,300 B2 | 11/2004 | Masini |
| 6,863,690 B2 | 3/2005 | Ball et al. |
| 6,875,234 B2 | 4/2005 | Lipman et al. |
| 6,893,702 B2 | 5/2005 | Takahashi |
| 6,896,702 B2 | 5/2005 | Collazo |
| 6,899,736 B1 | 5/2005 | Rauscher et al. |
| 6,911,047 B2 | 6/2005 | Rockwood, Jr. et al. |
| 6,942,699 B2 | 9/2005 | Stone et al. |
| 6,953,478 B2 | 10/2005 | Bouttens et al. |
| 7,011,686 B2 | 3/2006 | Ball et al. |
| 7,033,396 B2 | 4/2006 | Tornier |
| 7,051,451 B2 | 5/2006 | Augostino et al. |
| 7,090,677 B2 | 8/2006 | Fallin et al. |
| 7,160,328 B2 | 1/2007 | Rockwood, Jr. et al. |
| 7,160,331 B2 | 1/2007 | Cooney, III et al. |
| 7,169,184 B2 | 1/2007 | Dalla Pria |
| 7,175,665 B2 | 2/2007 | German et al. |
| 7,204,854 B2 | 4/2007 | Guederian et al. |
| 7,329,284 B2 | 2/2008 | Maroney et al. |
| 7,527,631 B2 | 5/2009 | Maroney et al. |
| 7,604,665 B2 | 10/2009 | Iannotti et al. |
| 7,608,109 B2 | 10/2009 | Dalla Pria |
| 7,621,961 B2 | 11/2009 | Stone |
| 7,625,408 B2 | 12/2009 | Gupta et al. |
| 7,753,959 B2 | 7/2010 | Berelsman et al. |
| 7,766,969 B2 | 8/2010 | Justin et al. |
| 7,892,287 B2 | 2/2011 | Deffenbaugh |
| 7,922,769 B2 | 4/2011 | Deffenbaugh et al. |
| 7,927,335 B2 | 4/2011 | Deffenbaugh et al. |
| 2001/0010636 A1 | 8/2001 | Gotou |
| 2001/0011192 A1 | 8/2001 | Ondrla et al. |
| 2001/0018589 A1 | 8/2001 | Muller |
| 2001/0030339 A1 | 10/2001 | Sandhu et al. |
| 2001/0037153 A1 | 11/2001 | Rockwood, Jr. et al. |
| 2002/0004685 A1 | 1/2002 | White |
| 2002/0082702 A1 | 6/2002 | Resch et al. |
| 2002/0099445 A1 | 7/2002 | Maroney et al. |
| 2003/0028253 A1 | 2/2003 | Stone et al. |
| 2003/0045883 A1 | 3/2003 | Chow et al. |
| 2003/0055507 A1 | 3/2003 | McDevitt et al. |
| 2003/0065397 A1 | 4/2003 | Hanssen et al. |
| 2003/0097183 A1 | 5/2003 | Rauscher et al. |
| 2003/0114933 A1 | 6/2003 | Bouttens et al. |
| 2003/0125809 A1 | 7/2003 | Iannotti et al. |
| 2003/0149485 A1 | 8/2003 | Tornier |
| 2003/0187514 A1 | 10/2003 | McMinn |
| 2004/0064189 A1 | 4/2004 | Maroney et al. |
| 2004/0122519 A1 | 6/2004 | Wiley et al. |
| 2004/0122520 A1 | 6/2004 | Lipman et al. |
| 2004/0162619 A1 | 8/2004 | Blaylock et al. |
| 2004/0193277 A1 | 9/2004 | Long et al. |
| 2004/0193278 A1 | 9/2004 | Maroney et al. |
| 2004/0220673 A1 | 11/2004 | Pria |
| 2004/0220674 A1 | 11/2004 | Pria |
| 2004/0230312 A1 | 11/2004 | Hanson et al. |
| 2004/0236424 A1 | 11/2004 | Berez et al. |
| 2005/0021148 A1 | 1/2005 | Gibbs |
| 2005/0049709 A1 | 3/2005 | Tornier |
| 2005/0125068 A1 | 6/2005 | Hozack et al. |
| 2005/0171613 A1 | 8/2005 | Sartorius et al. |
| 2005/0261775 A1 | 11/2005 | Baum et al. |
| 2006/0030946 A1 | 2/2006 | Ball et al. |
| 2006/0069443 A1 | 3/2006 | Deffenbaugh et al. |
| 2006/0069444 A1 | 3/2006 | Deffenbaugh |
| 2006/0074353 A1 | 4/2006 | Deffenbaugh et al. |
| 2006/0074430 A1 | 4/2006 | Deffenbaugh et al. |
| 2006/0079963 A1 | 4/2006 | Hansen |
| 2006/0100498 A1 | 5/2006 | Boyce et al. |
| 2006/0100714 A1 | 5/2006 | Ensign |
| 2006/0111787 A1 | 5/2006 | Bailie et al. |
| 2006/0142872 A1 | 6/2006 | Klotz et al. |
| 2006/0149387 A1 | 7/2006 | Smith et al. |
| 2006/0149388 A1 | 7/2006 | Smith et al. |
| 2006/0161260 A1 | 7/2006 | Thomas et al. |
| 2007/0055380 A1 | 3/2007 | Berelsman et al. |
| 2007/0142917 A1 | 6/2007 | Roche et al. |
| 2007/0179624 A1 | 8/2007 | Stone et al. |
| 2007/0219637 A1 | 9/2007 | Berelsman et al. |
| 2007/0219638 A1* | 9/2007 | Jones et al. ............... 623/19.11 |
| 2007/0225817 A1 | 9/2007 | Reubelt et al. |
| 2008/0046091 A1 | 2/2008 | Weiss et al. |
| 2008/0140209 A1 | 6/2008 | Iannotti et al. |
| 2008/0208348 A1 | 8/2008 | Fitz |
| 2008/0234820 A1 | 9/2008 | Felt et al. |

| | | | |
|---|---|---|---|
| 2009/0125113 A1 | 5/2009 | Guederian et al. | |
| 2009/0143865 A1 | 6/2009 | Hassler et al. | |
| 2009/0204225 A1 | 8/2009 | Meridew et al. | |
| 2009/0281630 A1 | 11/2009 | Delince et al. | |
| 2009/0292364 A1 | 11/2009 | Linares | |
| 2009/0312839 A1 | 12/2009 | Scheker et al. | |
| 2010/0049327 A1 | 2/2010 | Isch et al. | |
| 2010/0100190 A1* | 4/2010 | May et al. | 623/20.14 |

FOREIGN PATENT DOCUMENTS

| | | |
|---|---|---|
| DE | 102008021110 A1 | 10/2009 |
| EP | 0103246 A1 | 3/1984 |
| EP | 0329854 A1 | 8/1989 |
| EP | 0339530 A2 | 11/1989 |
| EP | 0538895 A2 | 4/1993 |
| EP | 0538895 A3 | 6/1993 |
| EP | 0581667 | 2/1994 |
| EP | 0776636 | 6/1997 |
| EP | 0903122 A2 | 3/1999 |
| EP | 1013246 | 6/2000 |
| EP | 1064890 | 1/2001 |
| EP | 1402853 | 3/2004 |
| EP | 1639966 A1 | 3/2006 |
| EP | 1639967 | 3/2006 |
| EP | 1902689 A1 | 3/2008 |
| EP | 1952788 A1 | 8/2008 |
| FR | 1064890 | 5/1954 |
| FR | 2578162 | 9/1986 |
| FR | 2579454 | 10/1986 |
| FR | 2652498 | 4/1991 |
| FR | 2683142 A1 | 5/1993 |
| FR | 2695313 A1 | 3/1994 |
| FR | 2704747 | 11/1994 |
| FR | 2755847 A1 | 5/1998 |
| FR | 2776506 A1 | 10/1999 |
| FR | 2825263 | 12/2002 |
| GB | 2297257 | 7/1996 |
| WO | 0134040 A1 | 5/2001 |
| WO | 02067821 A2 | 9/2002 |
| WO | 03005933 A2 | 1/2003 |
| WO | 03030770 A2 | 4/2003 |
| WO | 02067821 A3 | 8/2003 |
| WO | 03005933 A3 | 10/2003 |
| WO | 2007096741 | 8/2007 |
| WO | 2011098890 A1 | 8/2011 |

OTHER PUBLICATIONS

European Search Report in corresponding European patent application (i.e., EP 10 19 0436), completed Mar. 24, 2011 (2 pages).
European Search Report in corresponding European application (i.e., EP 09178360), dated May 12, 2010 (7 pages).
Biomet Corporation, Biomet Biomodular Low Profile Modular Glenoid, Surgical Technique, available at least as early as Dec. 22, 2008, one (1) page.
Biomet Corporation, Biangular Standard Metal Backed Glenoid, 1996, one (1) page.
Kirschner Medical Corporation, Kirschner Integrated Shoulder System for Hemi & Total Shoulder Arthroplasty, Surgical Technique, available at least as early as Dec. 22, 2008, two (2) pages.
Smith & Nephew Richards, Inc., The Cofield Total Shoulder System, available at least as early as Dec. 22, 2008, two (2) pages.
European Search Report in European application EP99304423, mailed Sep. 17, 1999, three (3) pages.

* cited by examiner

SHOULDER PROSTHESIS ASSEMBLY HAVING GLENOID RIM REPLACEMENT STRUCTURE

BACKGROUND

The present disclosure relates generally to shoulder prostheses, and more particularly to shoulder prostheses configured for use in shoulders having glenoid vault erosion or defects.

A typical shoulder or glenohumeral joint is formed in a human body where the humerus 10 movably contacts the scapula 12 as shown in FIG. 1. The scapula 12 includes a glenoid fossa 14 that forms a socket against which the head of the humerus 10 articulates. At this socket, the scapula 12 includes cartilage 16 that facilitates such articulation. Beneath the cartilage is subchondral bone 18 that forms a wall of a glenoid vault 20 that defines a cavity which contains cancellous bone 22. The subchondral bone 18 that forms the glenoid vault 20 defines a glenoid rim 21 at a periphery of the glenoid vault that is attached to the cartilage 16 (see FIG. 1). During the lifetime of a patient, the glenoid fossa 14 may become worn, especially at its posterior and/or superior portions thereby causing severe shoulder pain and limiting the range of motion of the patient's shoulder joint. To alleviate such pain and increase the patient's range of motion, a shoulder arthroplasty may be performed.

Shoulder arthroplasty often involves surgical replacement of the glenoid fossa with a conventional glenoid prosthesis such as the one disclosed in U.S. Pat. No. 6,911,047, the disclosure of which is herein incorporated by reference. The glenoid prosthesis, when implanted, provides a new laterally-facing bearing surface, which may be concave or convex, for articulation with a complementary bearing surface of a natural or prosthetic humeral head. Such conventional glenoid prosthesis is typically formed from UHMW polyethylene, titanium, or cobalt chrome and includes bone anchor(s) such as peg(s), screw(s), post(s), or a keel extending from a back side of the device opposite its bearing surface. So configured, the back side of the prosthesis is typically secured against subchondral bone of the glenoid vault while the bone anchor(s) may extend into the cavity of the glenoid vault whereby it may become anchored to cancellous bone located within the glenoid vault.

However, there are situations in which the subchondral bone support surface (including the glenoid rim) and underlying cancellous bone located within the glenoid vault may have become significantly deteriorated such that support and anchoring of a conventional glenoid prosthesis may be difficult. One such situation occurs when a patient experiences chronic subluxation of the shoulder that causes posterior erosion of the glenoid in which subchondral and cancellous bone of the glenoid is slowly worn away over time. Another such situation is seen when a conventional glenoid prosthesis is removed during a revision shoulder surgery. The removal of the conventional glenoid prosthesis reveals glenoid defects that were caused by repeated shoulder movement after the conventional shoulder prosthesis had become inadvertently loosened. Thus, in situations where there exists a significant amount of deterioration of the subchondral and cancellous bone, implantation of a conventional glenoid prosthesis described above may not be appropriate due to a lack of proper bone stock.

What is needed therefore is an improved prosthesis assembly for use in patients having deterioration of their subchondral support surface (including the glenoid rim) and underlying cancellous bone of their glenoid vault.

SUMMARY

In accordance with one embodiment of the present disclosure, there is provided a prosthesis assembly for use with a scapula. The prosthesis assembly includes a glenoid bearing support and a bearing. The glenoid bearing support includes a glenoid vault-occupying portion configured to occupy at least a portion of a glenoid vault of the scapula, the glenoid-vault occupying portion having a first coupling component. The glenoid bearing support further includes a glenoid rim replacement portion attached to the glenoid vault-occupying portion. The bearing defines a bearing surface and has a second coupling component configured to cooperate with the first coupling component to couple the bearing to the glenoid vault-occupying portion. The glenoid vault-occupying portion defines a bearing-side end portion and an opposite-side end portion. The glenoid rim replacement portion projects outwardly from the bearing-side end portion of the glenoid vault-occupying portion. The glenoid bearing support defines a bone graft receptacle.

Pursuant to another embodiment of the present disclosure, there is provided a shoulder prosthesis that includes a prosthesis assembly for use with a scapula. The prosthesis assembly includes a glenoid bearing support and bearing. The glenoid bearing support includes a glenoid vault-occupying portion configured to occupy at least a portion of a glenoid vault of the scapula, the glenoid-vault occupying portion defining a coupling recess. The glenoid bearing support also includes a glenoid rim replacement portion attached to the glenoid vault-occupying portion and positioned to surround the coupling recess. The bearing defines a bearing surface and has a coupling stem which is received within the coupling recess to couple the bearing to the glenoid vault-occupying portion. The glenoid vault-occupying portion defines a bearing-side end portion and an opposite-side end portion. The glenoid bearing support defines a bone graft receptacle located adjacent to the bearing-side end portion of the glenoid vault-occupying portion.

DESCRIPTION OF THE PREFERRED EMBODIMENTS

Figure 1:
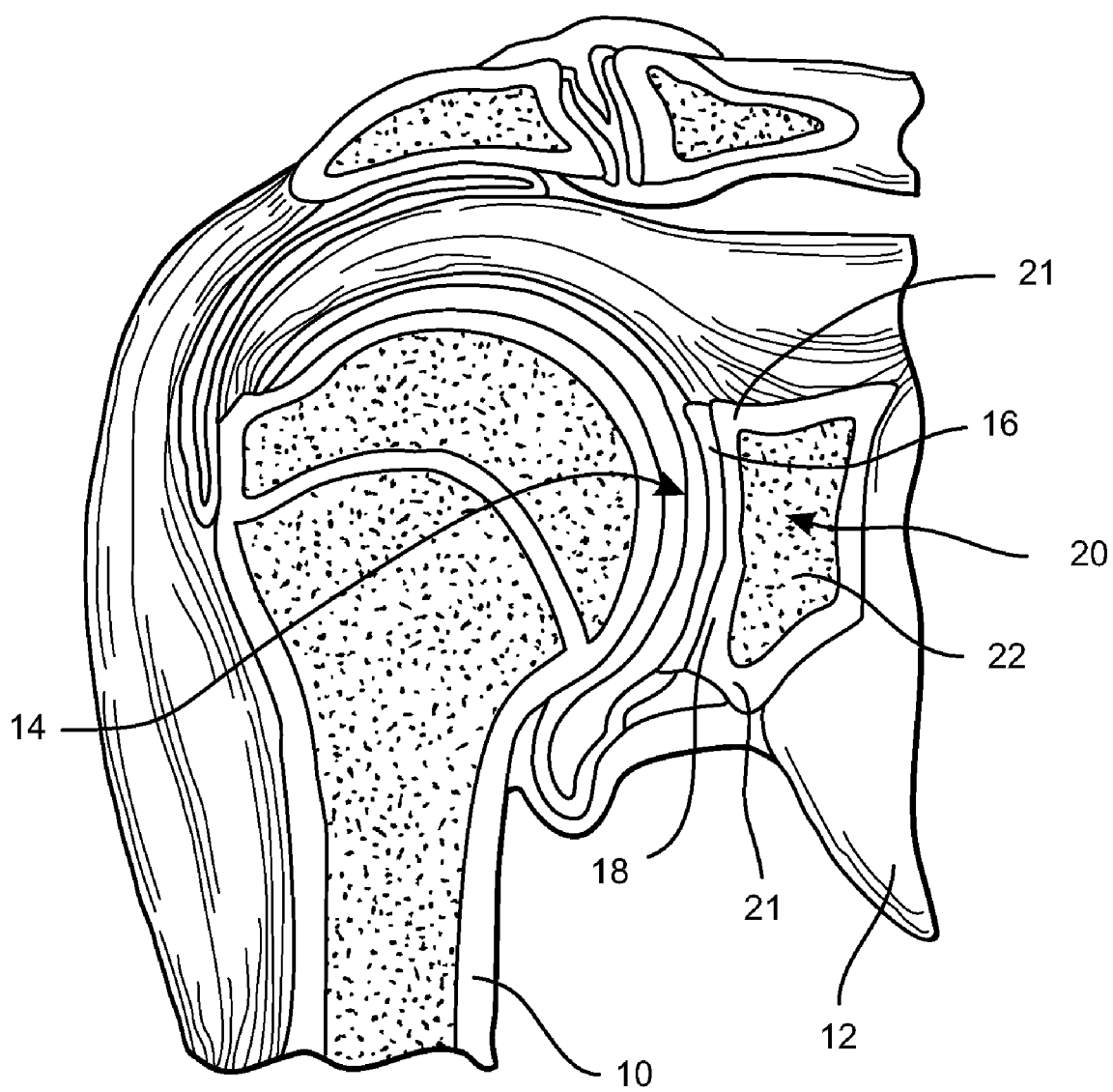
FIG. 1 is a cross-sectional view of an anatomically normal glenohumeral joint of a human patient.

While the shoulder prosthesis assembly described herein is susceptible to various modifications and alternative forms, specific embodiments thereof have been shown by way of example in the drawings and will herein be described in detail. It should be understood, however, that there is no intent to limit the shoulder prosthesis assembly to the particular forms disclosed, but on the contrary, the intention is to cover all modifications, equivalents, and alternatives falling within the spirit and scope of the invention as defined by the appended claims.

Figure 2:
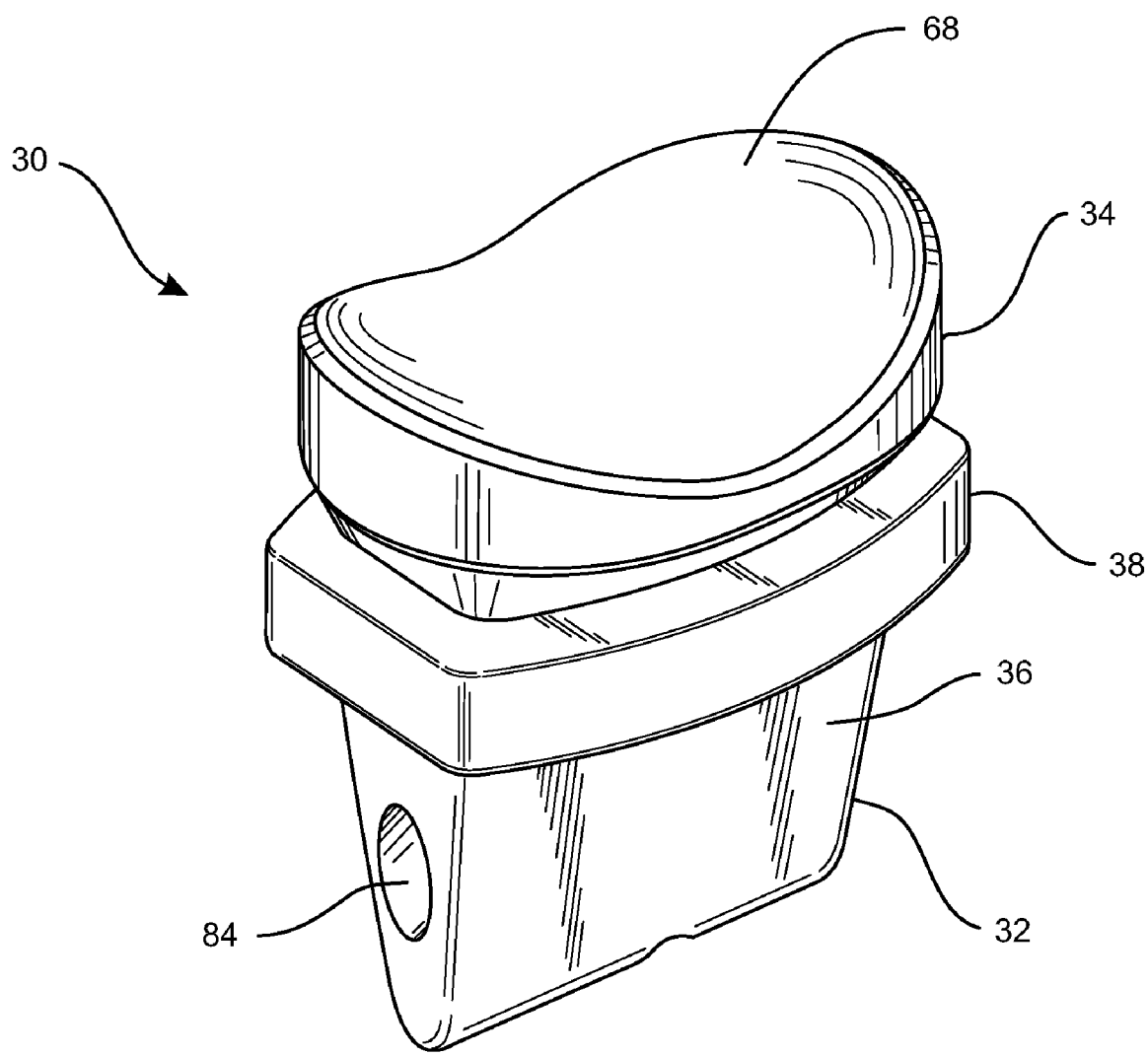
FIG. 2 is a perspective view of a shoulder prosthesis assembly of the present disclosure.

Referring now to FIG. 2, there is shown a shoulder prosthesis assembly 30 that is configured to be implanted in a human scapula. The prosthesis assembly 30 includes a glenoid bearing support 32 and a bearing 34. The glenoid bearing support 32 is made entirely of a metallic material, while the bearing 34 is made entirely of a polymeric material. Preferably, the glenoid bearing support 32 is made of a biological grade stainless steel or titanium material. Also, the glenoid bearing support may include a porous-coating on its entire outer surface to facilitate biological ingrowth of a patient's bone. The bearing 34 is preferably made entirely of a polymer such as polyethylene. One particular polyethylene that is well suited for use as the bearing component is a high molecular weight polyethylene, for example, ultra-high molecular weight polyethylene (UHMWPE).

The glenoid bearing support 32 is shown in more detail in FIGS. 3-7. In particular, the glenoid bearing support 32 includes a glenoid vault-occupying portion 36 and a glenoid rim replacement portion 38. The glenoid rim replacement portion 38 is attached to the glenoid vault-occupying portion 36 as shown in FIGS. 3-7. Preferably, the glenoid rim replacement portion 38 and the glenoid vault-occupying portion 36 are attached to each other by being integrally formed together as a single part. Alternatively, the glenoid rim replacement portion 38 and the glenoid vault-occupying portion 36 may be attached to each other by these portions possessing complementary snap-fit or friction-fit features or the like.

Figure 3:
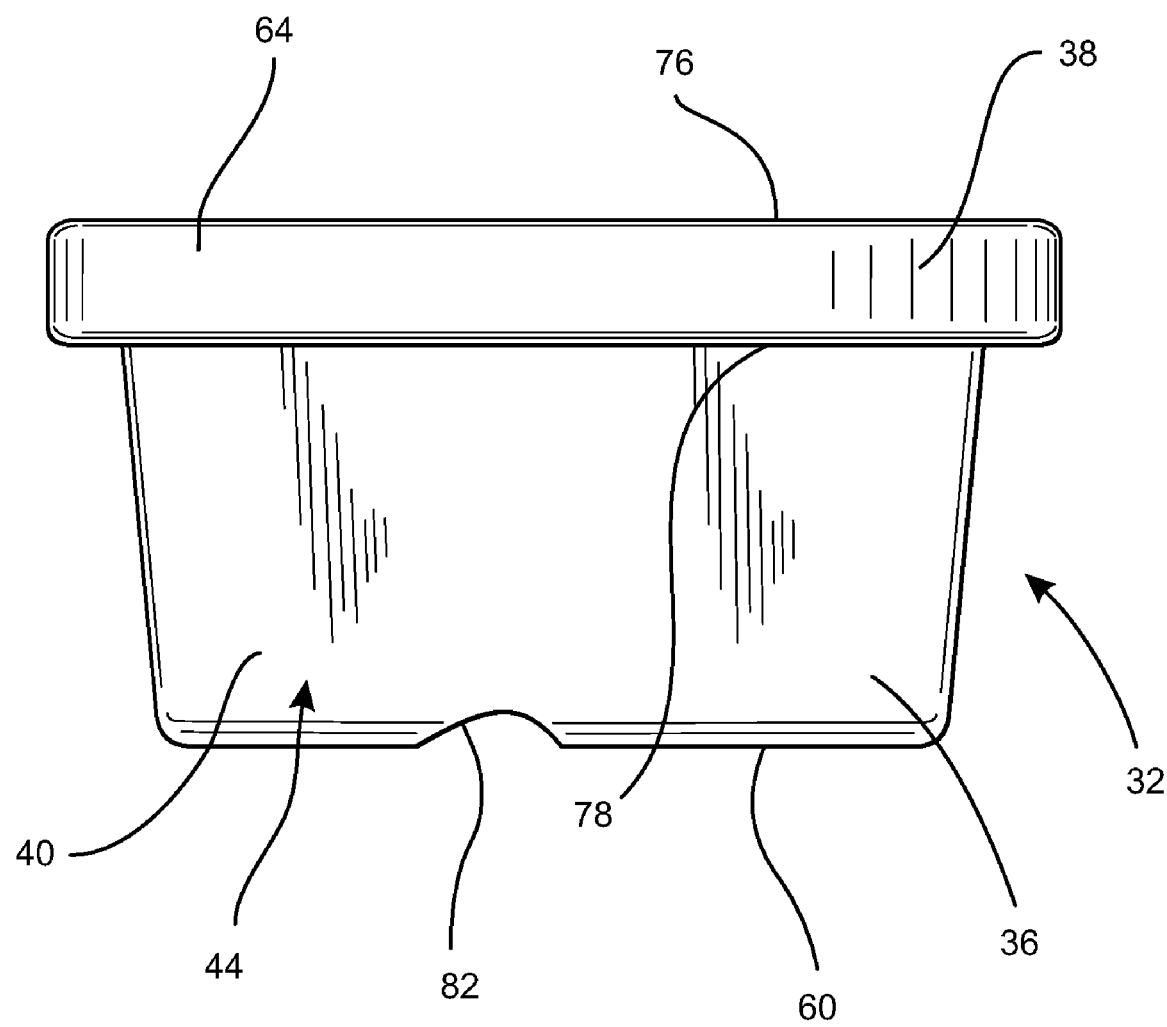
FIG. 3 is a side elevational view of the glenoid bearing support of the shoulder prosthesis of FIG. 2.
Figure 4:
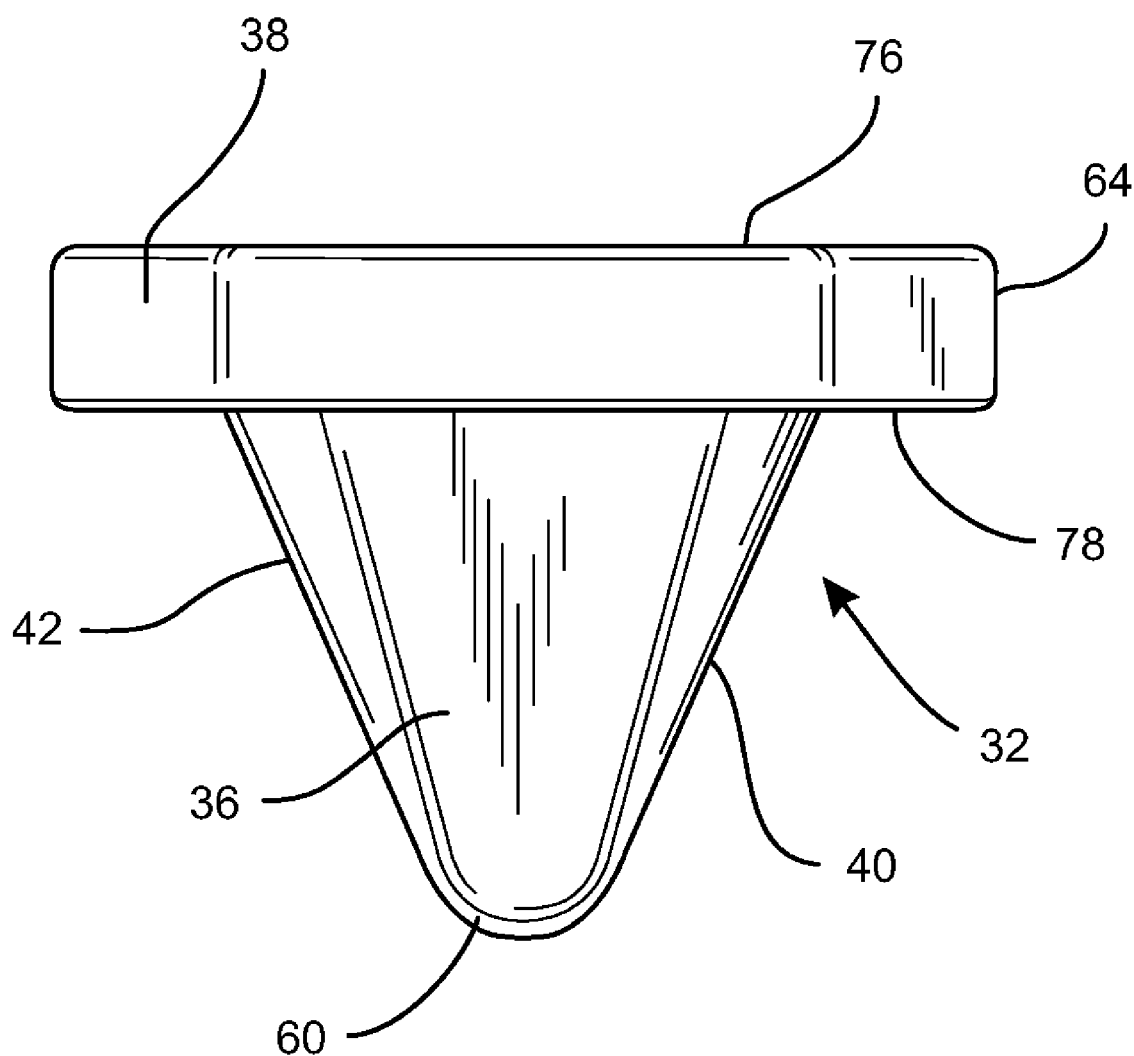
FIG. 4 is an end elevational view of the glenoid bearing support of the shoulder prosthesis of FIG. 2.
Figure 7:
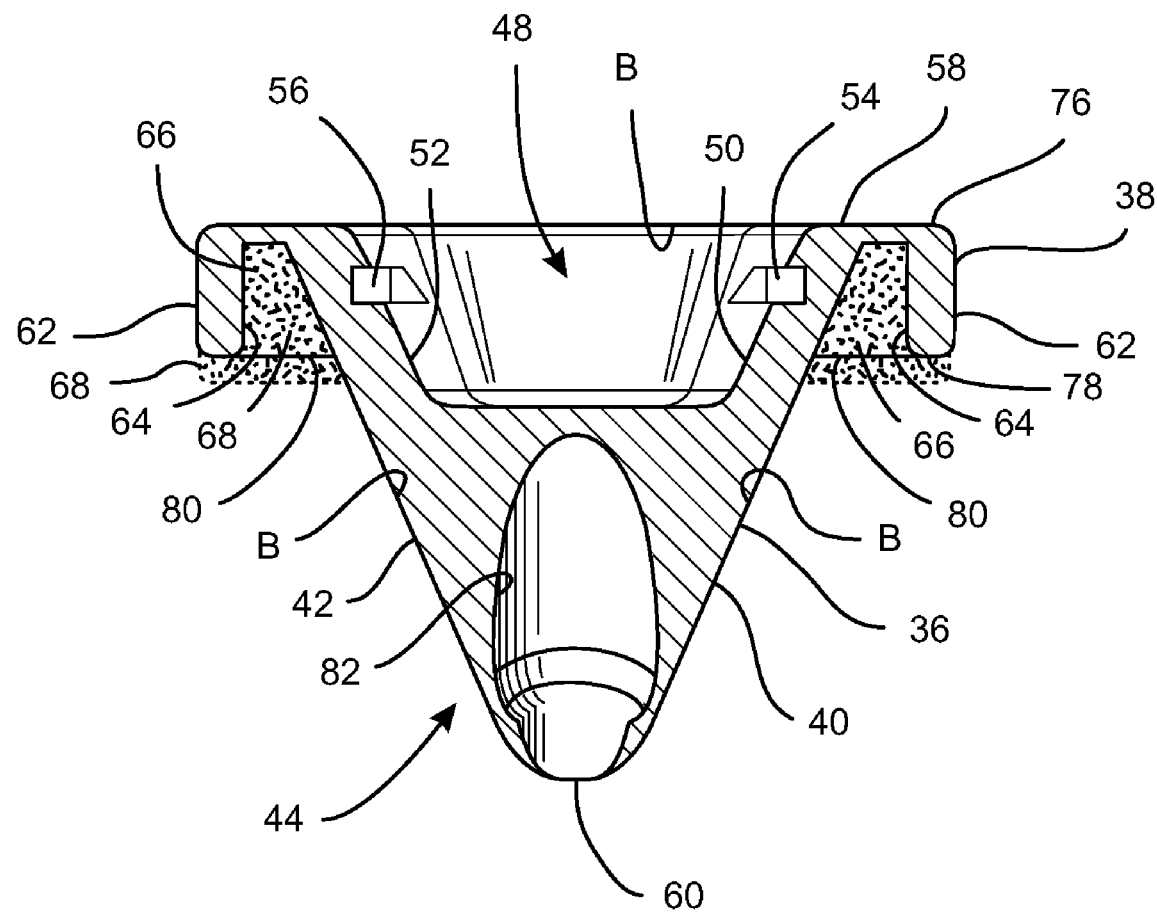
FIG. 7 is cross-sectional view of the glenoid bearing support taken along the lines 7-7 of FIG. 5.

The glenoid vault-occupying portion 36 is configured to occupy at least a portion of the glenoid vault of a scapula, such as glenoid vault 20 shown in FIG. 1. Preferably, the glenoid vault-occupying portion 36 is configured to substantially completely fill the glenoid vault of a scapula, such as glenoid vault 20 shown in FIG. 1. To this end, the glenoid vault-occupying portion 36 has an exterior wall 40 and an exterior wall 42 as best shown in FIGS. 3, 4, and 7. When the glenoid vault-occupying portion 36 is viewed in cross-section (see FIG. 7) the exterior wall 40 and the exterior wall 42 are positioned with respect to each other to define a generally V-shaped exterior wall 44. The generally V-shaped exterior wall 44 defines a boundary B which is occupied in part by structure of the glenoid vault-occupying portion 36.

Figure 5:
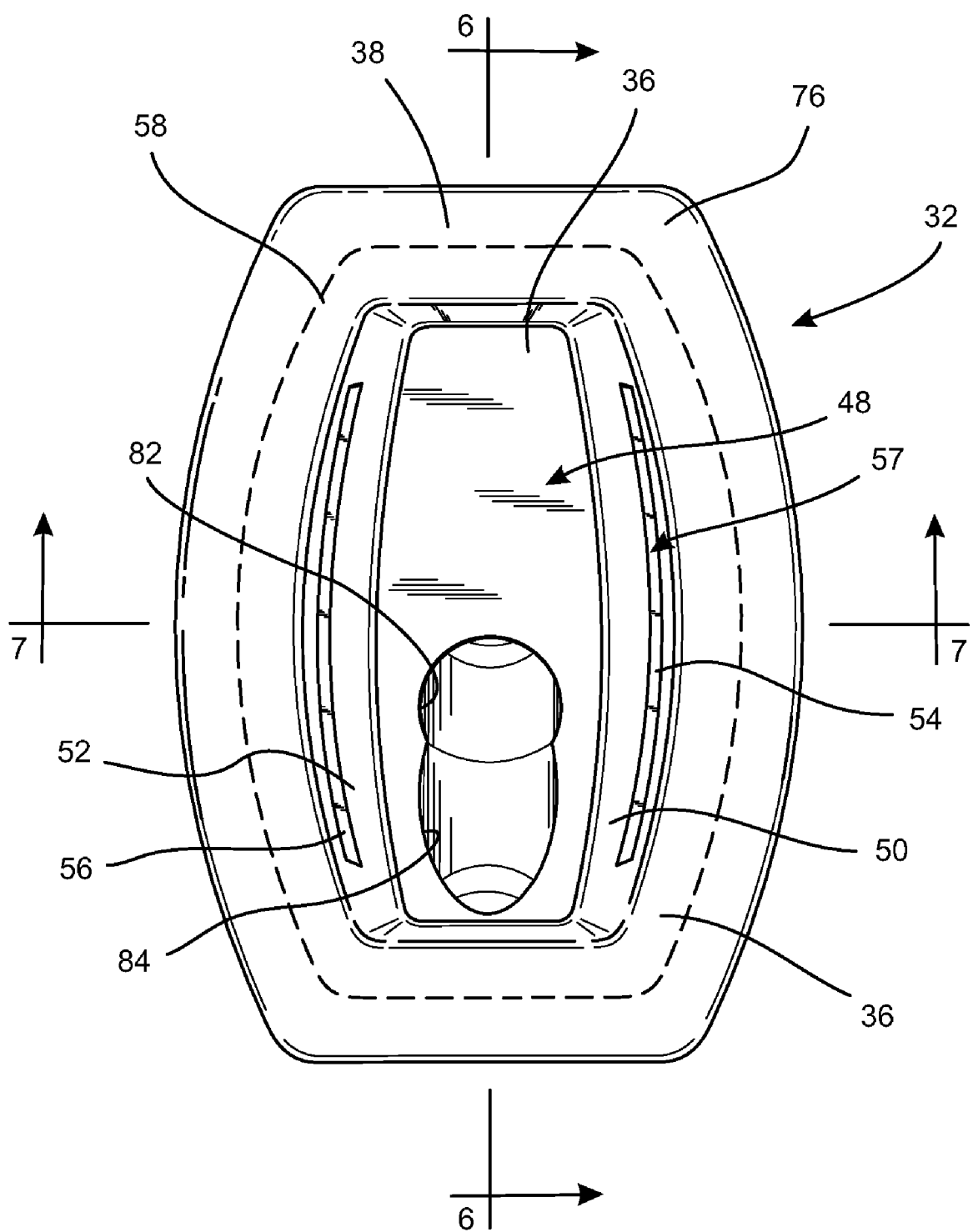
FIG. 5 is a top elevational view of the glenoid bearing support of the shoulder prosthesis of FIG. 2.
Figure 6:
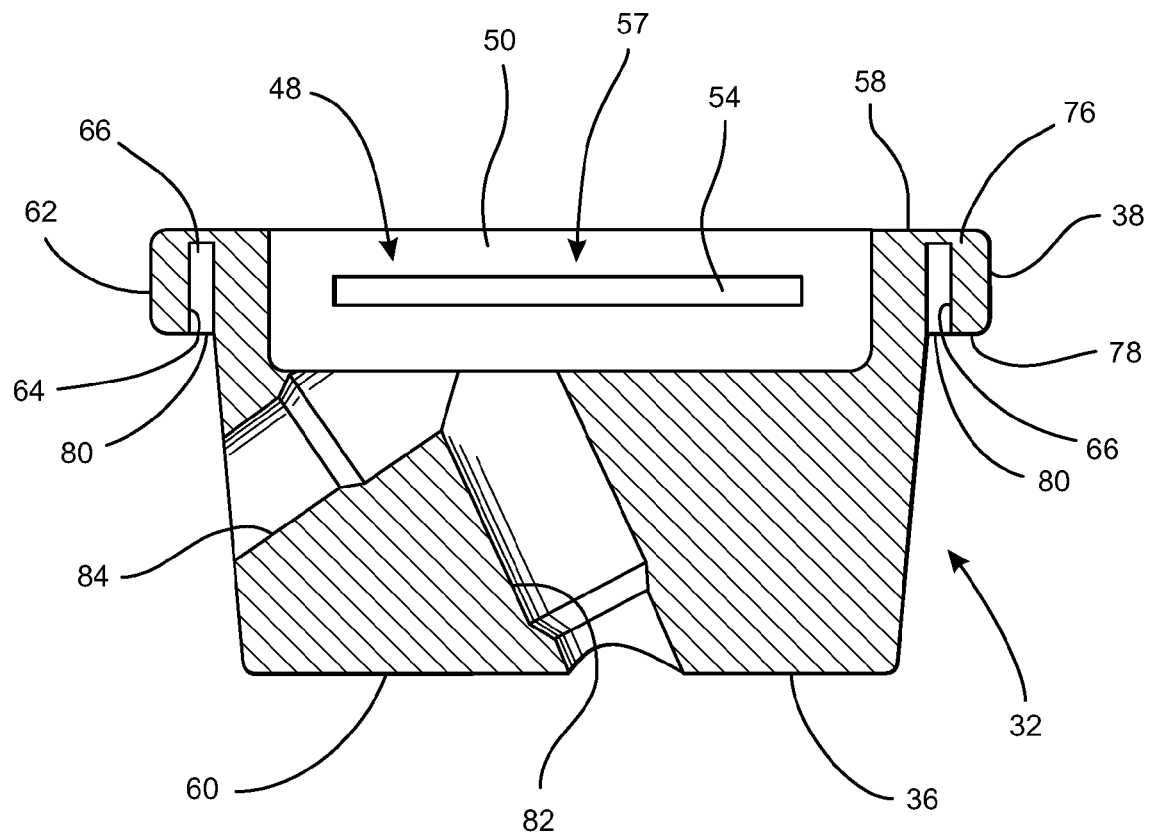
FIG. 6 is cross-sectional view of the glenoid bearing support taken along the lines 6-6 of FIG. 5.

The glenoid vault-occupying portion 36 has a coupling recess 48 defined therein as shown in FIGS. 5-7. The coupling recess 48 is defined by a tapered interior surface 50 and a tapered interior surface 52. The tapered interior surface 50 has a slot 54 defined therein, while the tapered interior surface 52 has a slot 56 defined therein. The tapered interior surface 50, the slot 54, the tapered interior surface 52, and the slot 56 collectively define a coupling component 57.

The glenoid vault-occupying portion 36 defines a bearing-side end portion 58 and an opposite side end portion 60 as shown in FIGS. 6-7. The glenoid rim replacement portion 38 projects outwardly from the bearing-side end portion 58 as in FIGS. 5-7. The glenoid rim replacement portion 38 is configured to surround the bearing-side end portion of the glenoid vault-occupying portion 36 as shown in FIG. 5. The glenoid rim replacement portion 38 is also configured to surround the coupling recess 48 and the coupling component 57 as shown in FIG. 5.

The glenoid rim replacement portion 38 includes an exterior surface 62 and an interior surface 64. The interior surface 64 of the glenoid replacement portion 38 faces the exterior wall 40 of the glenoid vault-occupying portion 36 as shown in FIG. 7. The interior surface 64 of the glenoid rim replacement portion 38 and the exterior wall 40 of the glenoid vault-occupying portion 36 defines a bone graft receptacle 66 as shown in FIG. 7. The bone graft receptacle 66 is configured to receive a quantity of bone graft material 65 therein. FIG. 7 shows the quantity of bone graft material 65 positioned in the bone graft receptacle 66. Additional bone graft material 65 is also located outside of the bone graft receptacle 66 as shown in FIG. 7. The bone graft material 65 includes cortical bone graft material and/or cancellous bone graft material. The bone graft material 65 is preferably packed or compressed into the bone graft receptacle 66. It should be appreciated that the bone graft receptacle 66 is located outside of the boundary B as shown in FIG. 7.

Figure 19:
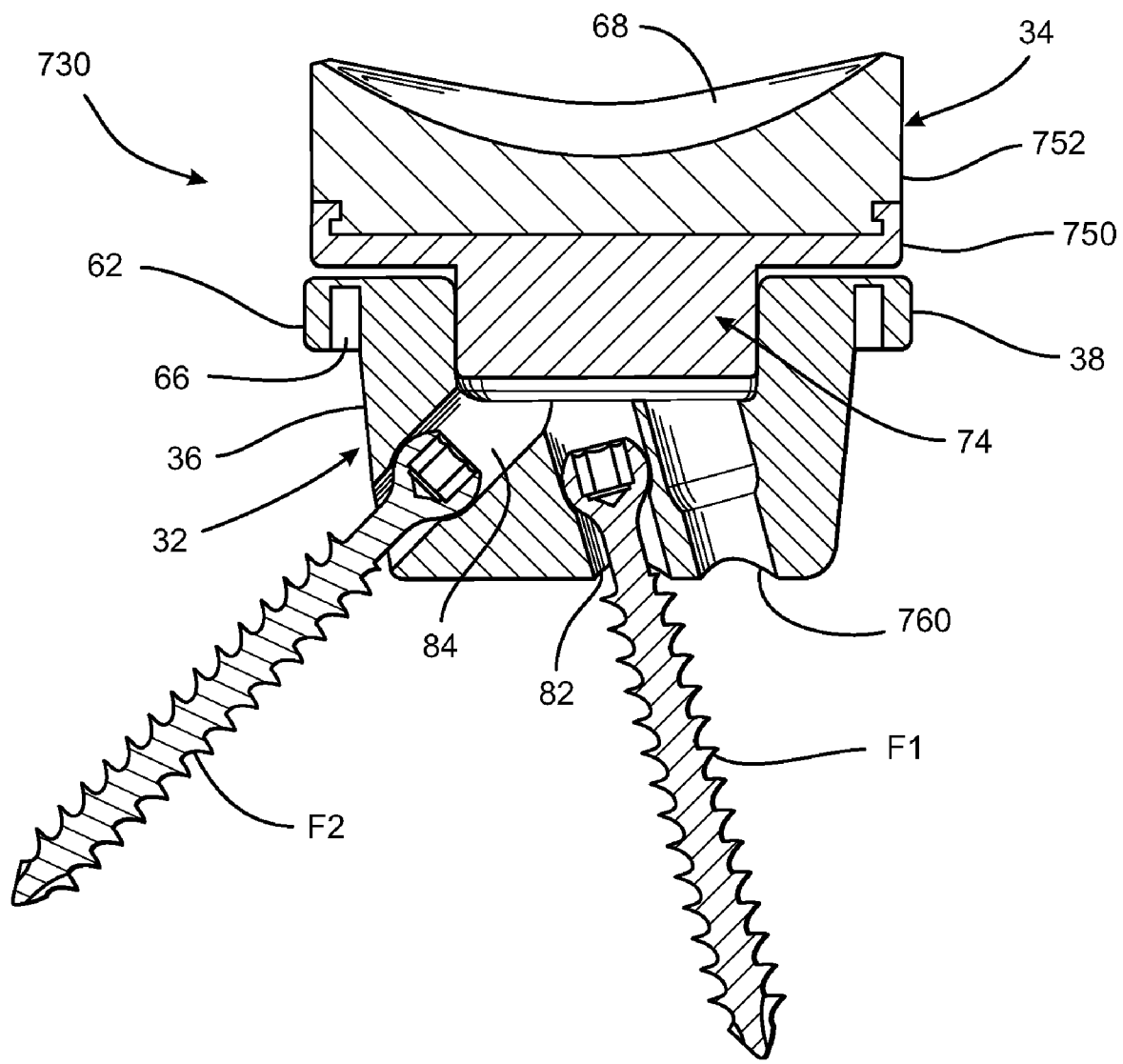
FIG. 19 is a perspective view of yet another alternative embodiment of a shoulder prosthesis assembly of the present disclosure.

The glenoid vault-occupying portion 36 further includes a fastener channel 82 and another fastener channel 84 as best shown in FIG. 6. Fasteners are positioned in the fastener channels 82, 84 such as shown in FIG. 19 so as to facilitate initial fixation.

The glenoid rim replacement portion 38 defines a bearing-facing side 76 and a scapula-facing side 78 as shown in FIGS. 6-7. The glenoid bearing support 32 further defines an access opening 80 configured to allow bone graft material to be advanced therethrough to the bone graft receptacle 66. The access opening 80 is positioned adjacent to the scapula-facing side 78 of the glenoid rim replacement portion 38 as shown in FIGS. 6-7. The access opening 80 surrounds the glenoid vault-occupying portion 36.

Figure 8:
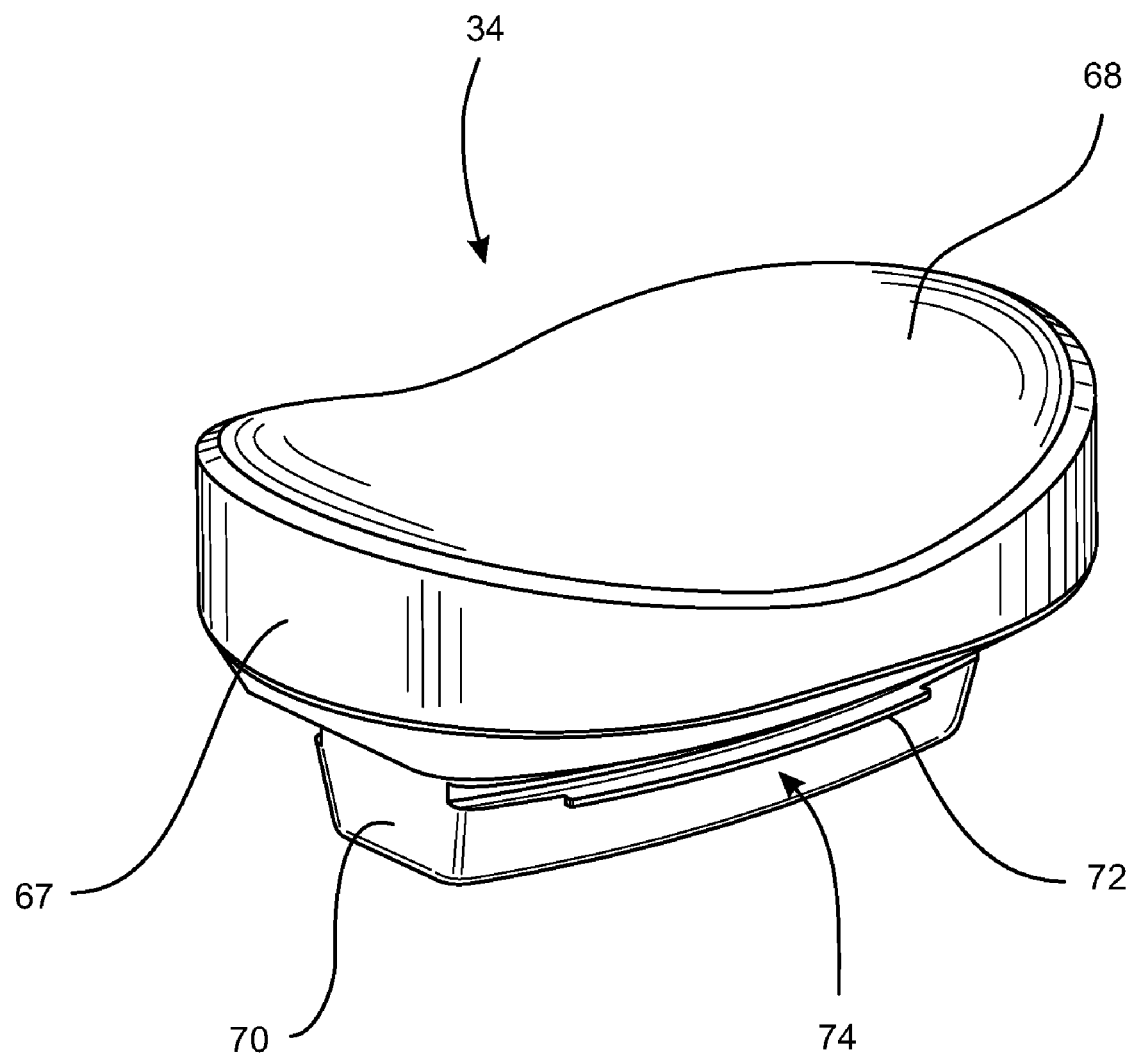
FIG. 8 is a perspective view of the bearing of the shoulder prosthesis of FIG. 2.
Figure 9:
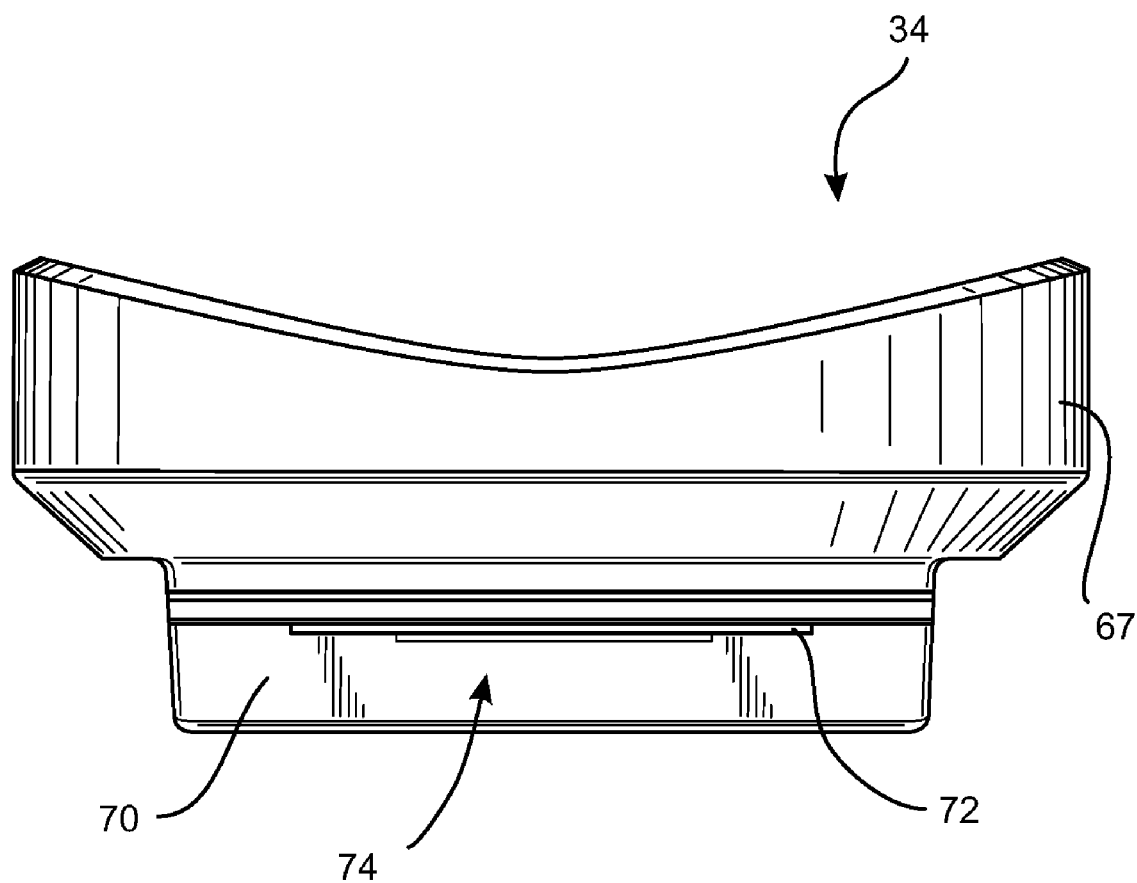
FIG. 9 is a side elevational view of the bearing of the shoulder prosthesis of FIG. 2.
Figure 10:
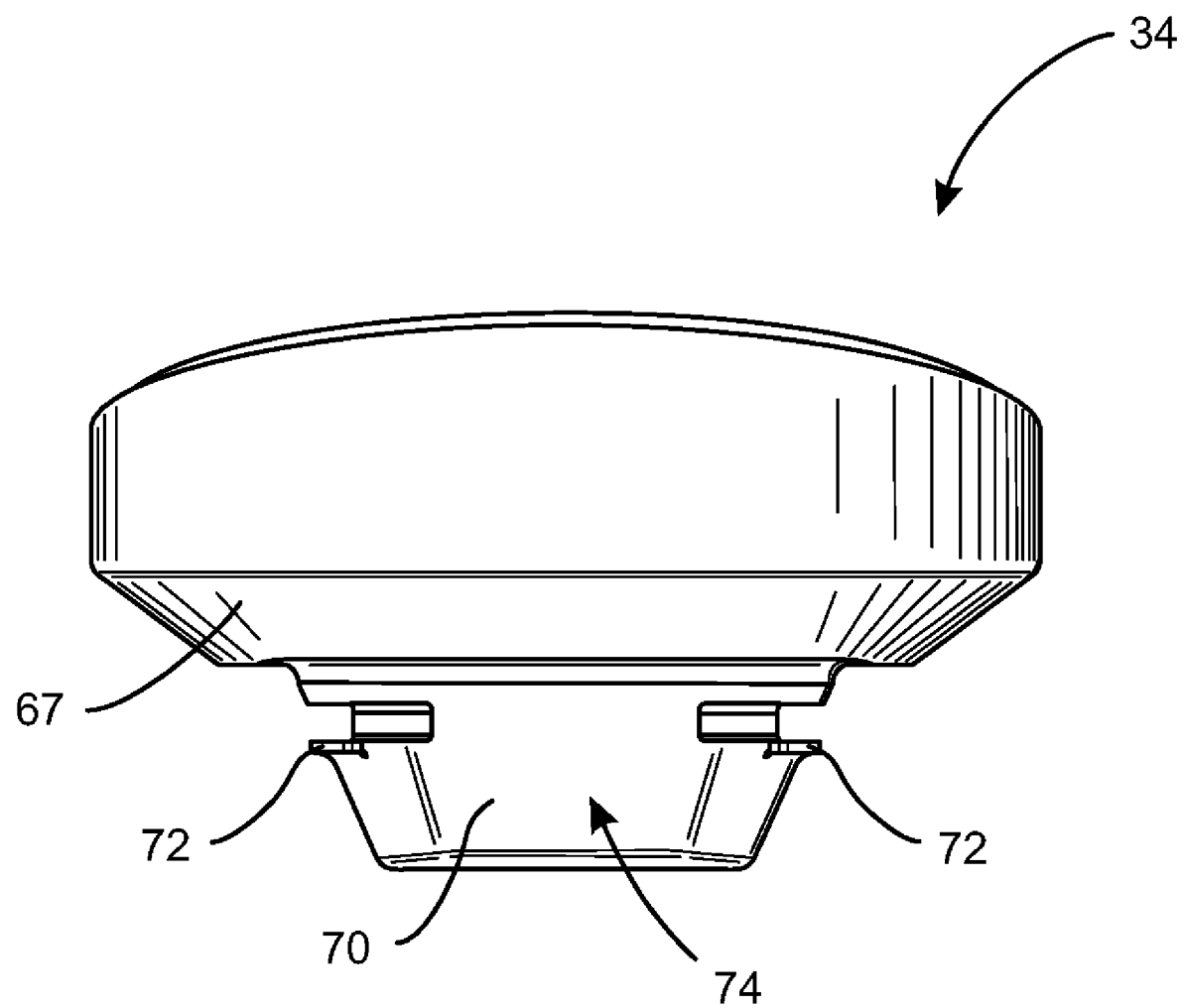
FIG. 10 is an end elevational view of the bearing of the shoulder prosthesis of FIG. 2.

The bearing 34 is shown in more detail in FIGS. 8-10. In particular, the bearing 34 includes a body 67 defining a bearing surface 68. The bearing surface 68 is a concave bearing surface as shown in FIGS. 2 and 8. The bearing 34 further includes a connector member 70 extending downwardly from the body 67 as shown in FIGS. 8-10. The connector member 70 includes two outwardly extending tabs 72. The connector member 70 including tabs 72 define a coupling component 74 configured to cooperate with the coupling component 57 of the glenoid vault-occupying portion 36 so as to couple the bearing 34 to the glenoid vault-occupying portion 36. In particular, the connector member 70 is configured to be received within the coupling recess 48 of the glenoid vault-occupying portion 36. When the connector member 70 is received as such, the tabs 72 of the connector member 70 are respectively received within the slots 54, 56 defined in the tapered interior surfaces 50, 52.

Figure 11:
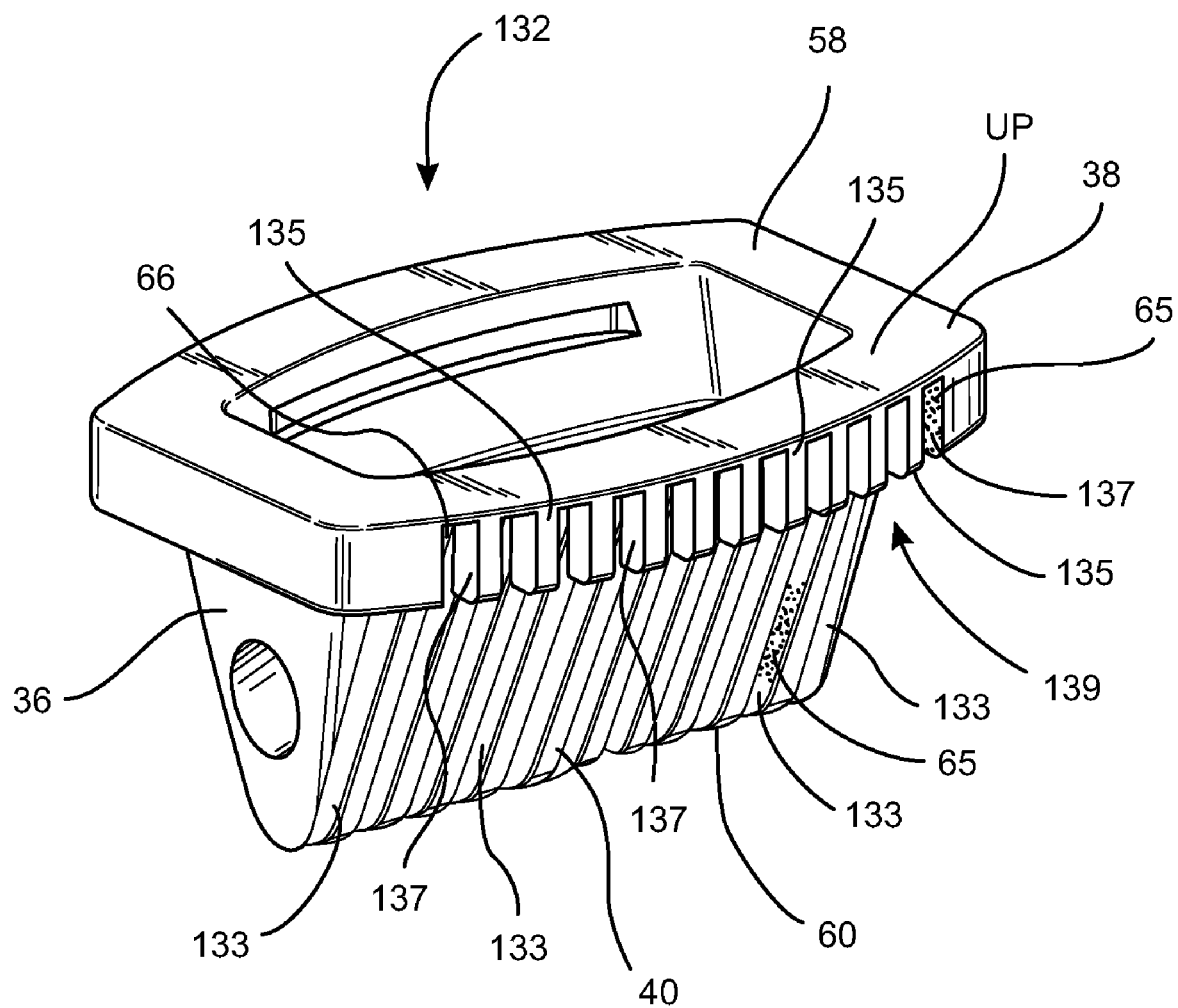
FIG. 11 is a perspective view of an alternative embodiment of the glenoid bearing support which may be used in the shoulder prosthesis of FIG. 2 in place of the glenoid bearing support therein.

Turning now to FIG. 11, there is shown another embodiment of a glenoid bearing support 132. The glenoid bearing support 132 is used in substantially the same manner as the glenoid bearing support 32 described herein. In addition, the glenoid bearing support 32 possesses the exact same dimensions and configuration as the glenoid bearing support 132, with two exceptions. Thus, the reference numbers utilized to identify features of the glenoid bearing support 32 are utilized in FIG. 11 to identify like features of the glenoid bearing support 132.

The first exception relates to the exterior walls 40, 42 of the glenoid vault-occupying portion 36 of the glenoid bearing support 132. In particular, the exterior walls 40, 42 have defined therein a plurality of vertically extending grooves 133 that extend from the opposite-side end portion 60 to the bearing side end portion 58 as shown in FIG. 11. The vertically extending grooves 133 are configured to receive a quantity of bone graft material 65 therein. FIG. 11 shows the quantity of bone graft material 65 positioned in the vertically extending grooves 133.

The second exception relates to the glenoid rim replacement portion 38 of the glenoid bearing support 132. More specifically, the glenoid rim replacement portion 38 has a plurality of vertically aligned ribs 135 extending downwardly from an upper portion UP thereof. The plurality of vertically aligned ribs 135 define a plurality of vertically aligned slots 137 as shown in FIG. 11. Each of the slots 137 communicate with the bone graft receptacle 66. The slots 137 collective comprise another bone graft receptacle 139, with each slot defining a sub-receptacle for receiving a quantity of bone graft material 65 therein. Note that while only one side portion of the glenoid rim replacement portion 38 of the glenoid bearing support 132 is shown in detail possessing the ribs 135 and slots 137 (front side in FIG. 11), it should be appreciated that the other side portion of the glenoid rim replacement portion 38 of the glenoid bearing support 132 (back side in FIG. 11) also possesses identical ribs 135 and slots 137 as well.

Figure 12:
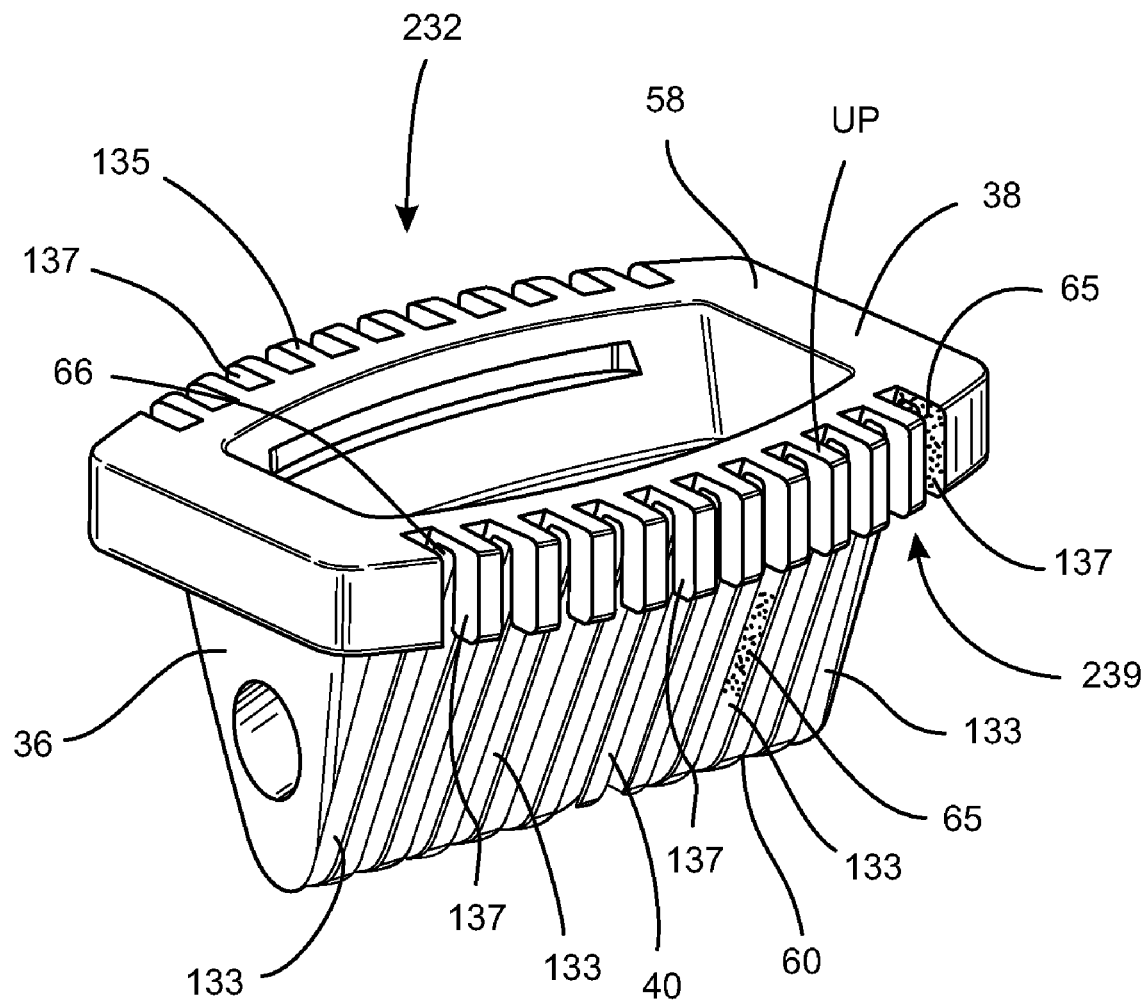
FIG. 12 is a perspective view of yet another alternative embodiment of the glenoid bearing support which may be used in the shoulder prosthesis of FIG. 2 in place of the glenoid bearing support therein.

Turning now to FIG. 12, there is shown yet another embodiment of a glenoid bearing support 232. The glenoid bearing support 232 is used in substantially the same manner as the glenoid bearing support 132 described herein. In addition, the glenoid bearing support 132 possesses the exact same dimensions and configuration as the glenoid bearing support 232, with one exception. Thus, the reference numbers utilized to identify features of the glenoid bearing support 132 are utilized in FIG. 12 to identify like features of the glenoid bearing support 232.

The exception relates to the glenoid rim replacement portion 38 of the glenoid bearing support 232, and in particular, the ribs 135 and slots 137 of thereof. In particular, the plurality of vertically aligned slots 137 extend all the way vertically through the upper portion UP of the glenoid rim replacement portion 38 as shown in FIG. 12. Thus, the ribs 135 are configured to be L-shaped thereby providing the bone graft receptacle 239 with more space to receive additional bone graft material therein.

Figure 13:
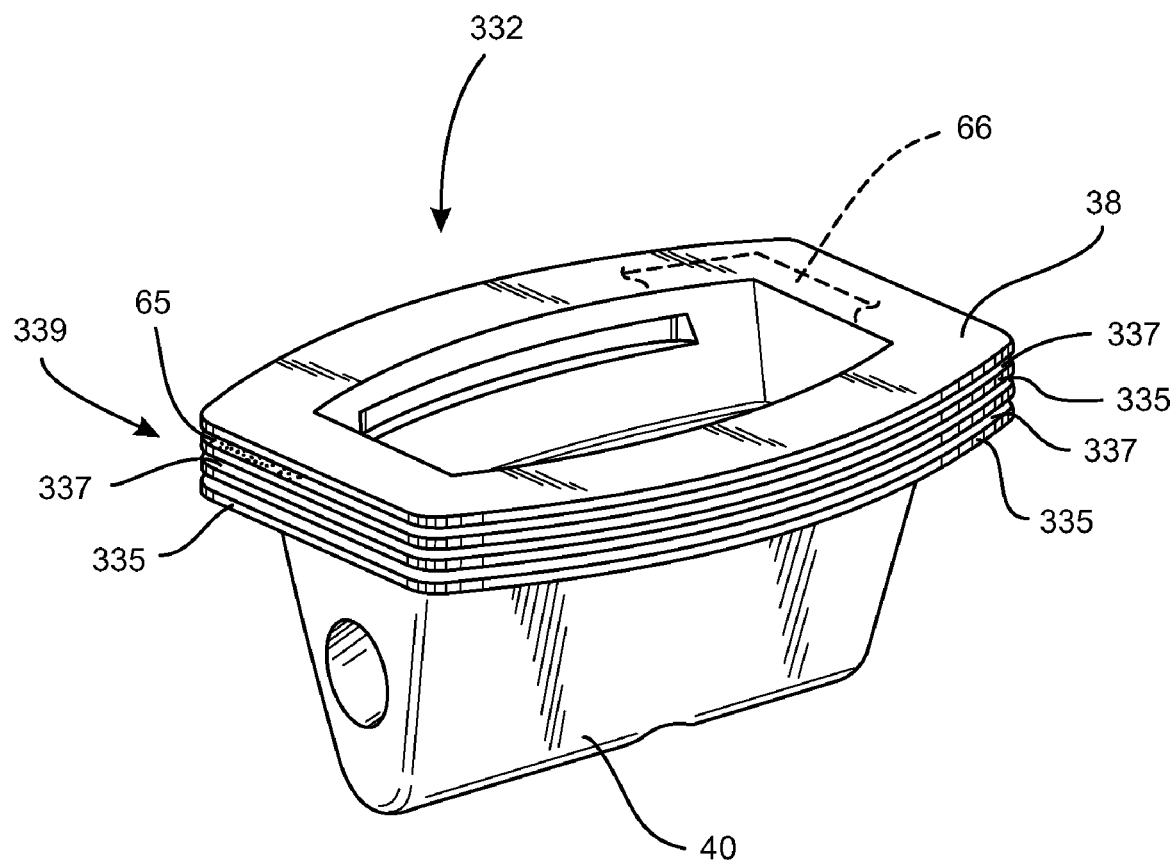
FIG. 13 is a perspective view of still another alternative embodiment of the glenoid bearing support which may be used in the shoulder prosthesis of FIG. 2 in place of the glenoid bearing support therein.

Turning now to FIG. 13, there is shown another embodiment of a glenoid bearing support 332. The glenoid bearing support 332 is used in substantially the same manner as the glenoid bearing support 32 described herein. In addition, the glenoid bearing support 32 possesses the exact same dimensions and configuration as the glenoid bearing support 132, with one exception. Thus, the reference numbers utilized to identify features of the glenoid bearing support 32 are utilized in FIG. 13 to identify like features of the glenoid bearing support 332.

The exception relates to the glenoid rim replacement portion 38 of the glenoid bearing support 332. More specifically, the glenoid rim replacement portion 38 has a plurality of horizontally aligned ribs 335 extending around the glenoid rim replacement portion 38 of the glenoid bearing support 332. The plurality of horizontally aligned ribs 335 define a plurality of horizontally aligned slots 337 as shown in FIG. 13. In contrast to the embodiment shown in FIGS. 11-12, each of the slots 337 do not communicate with the bone graft receptacle 66. The slots 337 collective comprise another bone graft receptacle 339, with each slot defining a sub-receptacle for receiving a quantity of bone graft material 65 therein. Note that while only one side portion of the glenoid rim replacement portion 38 of the glenoid bearing support 332 is shown in detail possessing the ribs 335 and slots 337 (front side in FIG. 13), it should be appreciated that the other side portion of the glenoid rim replacement portion 38 of the glenoid bearing support 332 (back side in FIG. 13) also possesses identical ribs 335 and slots 337 as well. The slots 337 collective comprise another bone graft receptacle 339, with each slot defining a sub-receptacle for receiving a quantity of bone graft material 65 therein.

Figure 14:
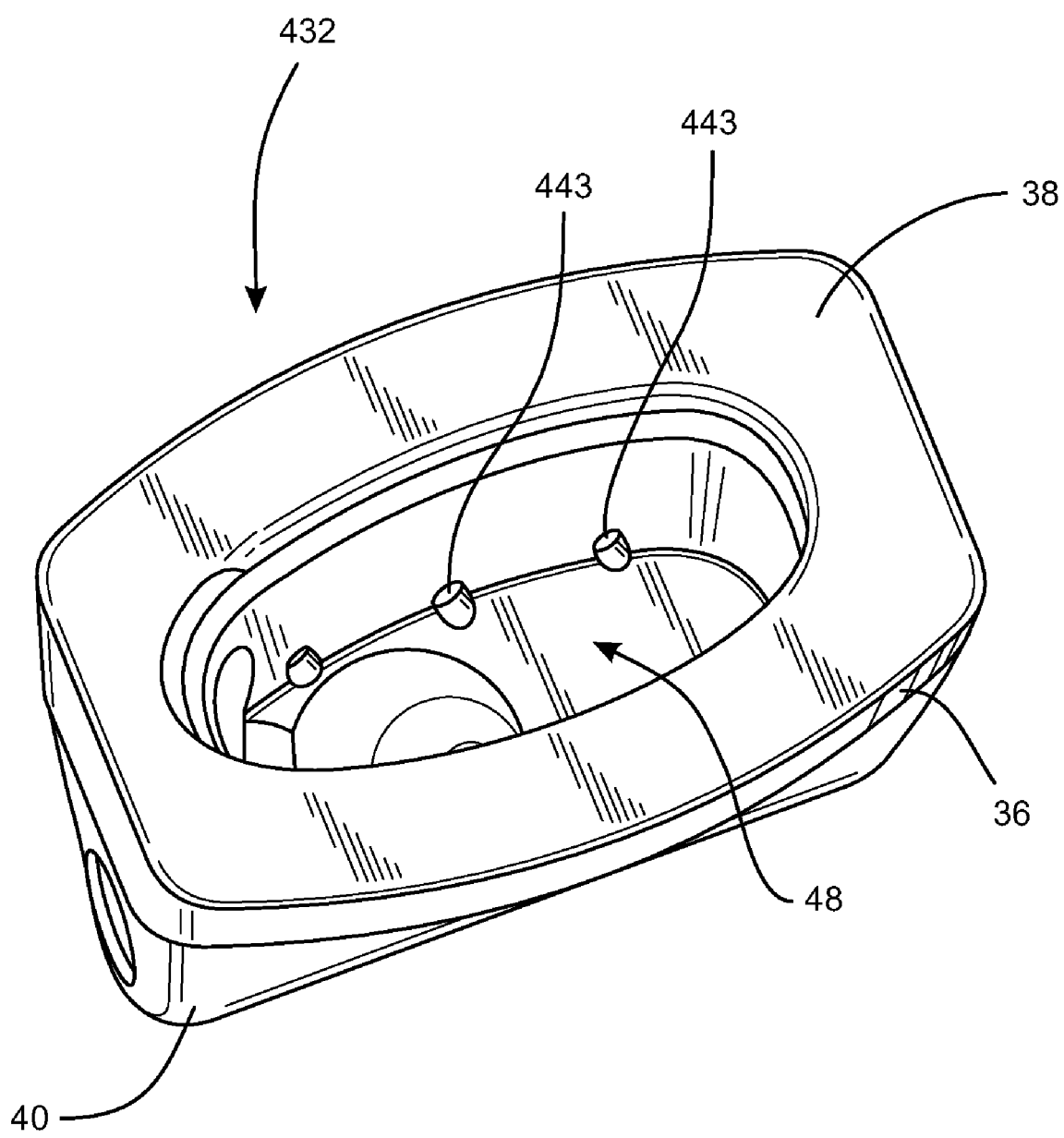
FIG. 14 is a perspective view of yet a further alternative embodiment of the glenoid bearing support which may be used in the shoulder prosthesis of FIG. 2 in place of the glenoid bearing support therein.

Turning now to FIG. 14, there is shown another embodiment of a glenoid bearing support 432. The glenoid bearing support 432 is used in substantially the same manner as the glenoid bearing support 32 described herein. In addition, the glenoid bearing support 32 possesses the exact same dimensions and configuration as the glenoid bearing support 432, with one exception. Thus, the reference numbers utilized to identify features of the glenoid bearing support 32 are utilized in FIG. 14 to identify like features of the glenoid bearing support 432.

The exception relates to side walls f the glenoid vault-occupying portion 36 of the glenoid bearing support 432 that include exterior walls 40, 42. In particular, the side walls have defined therein a plurality of suture holes 443 that extend through the walls as shown in FIG. 14. The suture holes 443 are configured to receive suture therethrough so as to secure a quantity of bone graft material to the glenoid bearing support 432.

Figure 15:
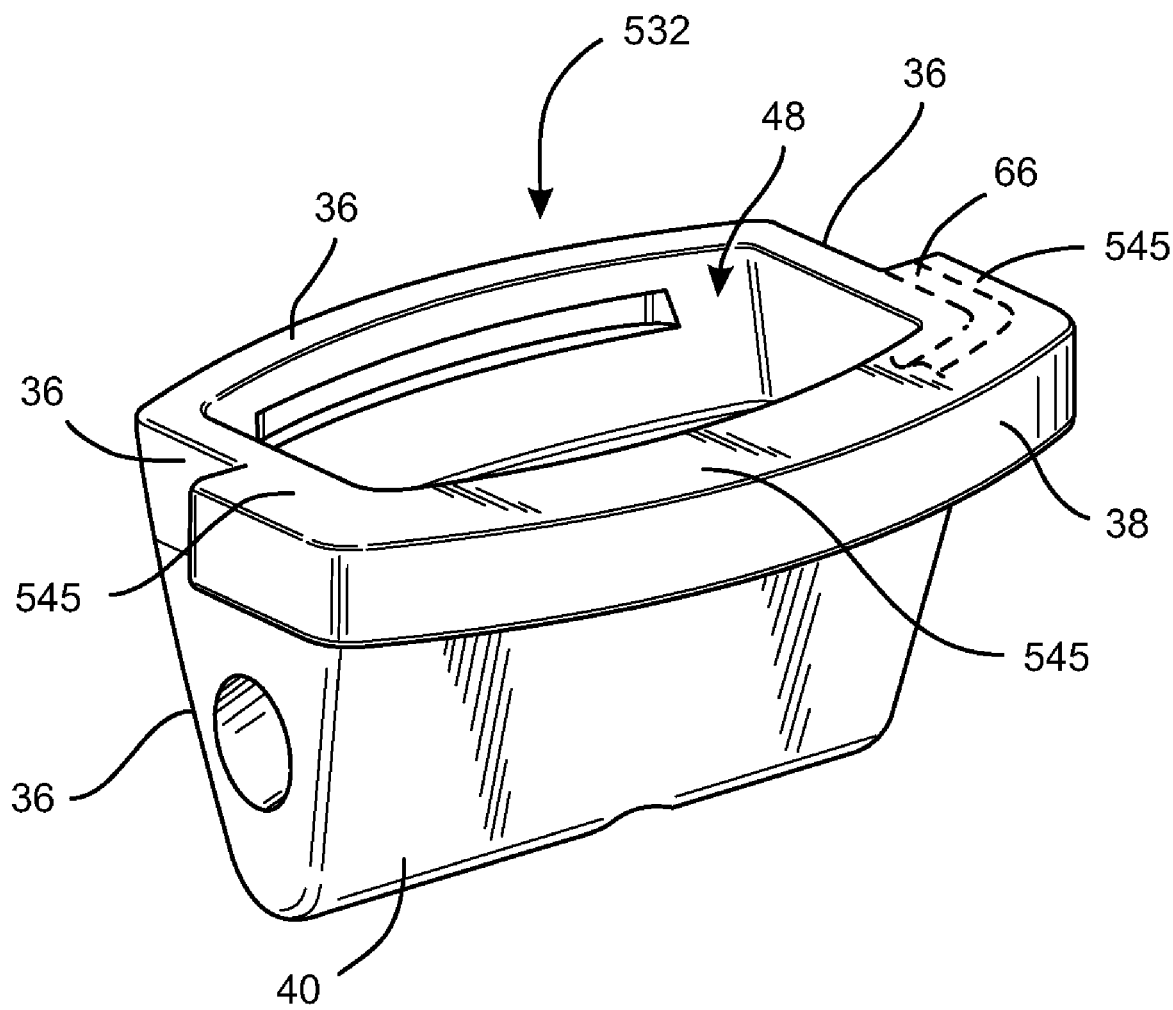
FIG. 15 is a perspective view of still another alternative embodiment of the glenoid bearing support which may be used in the shoulder prosthesis of FIG. 2 in place of the glenoid bearing support therein.

Turning now to FIG. 15, there is shown another embodiment of a glenoid bearing support 532. The glenoid bearing support 532 is used in substantially the same manner as the glenoid bearing support 32 described herein. In addition, the glenoid bearing support 32 possesses the exact same dimensions and configuration as the glenoid bearing support 532, with one exception. Thus, the reference numbers utilized to identify features of the glenoid bearing support 32 are utilized in FIG. 15 to identify like features of the glenoid bearing support 532.

The exception relates to the glenoid rim replacement portion 38 of the glenoid bearing support 532. In particular, the glenoid rim replacement portion 38 of the glenoid bearing support 532 includes a rim segment 545 that extends only part-way around the glenoid vault-occupying portion 36. In this embodiment, the glenoid rim replacement portion 38 preferably extends only half-way around the periphery of the glenoid vault-occupying portion 36 as shown in FIG. 15. As a result, the bone graft receptacle 66 likewise only extends only half-way around the glenoid vault-occupying portion 36.

Figure 16:
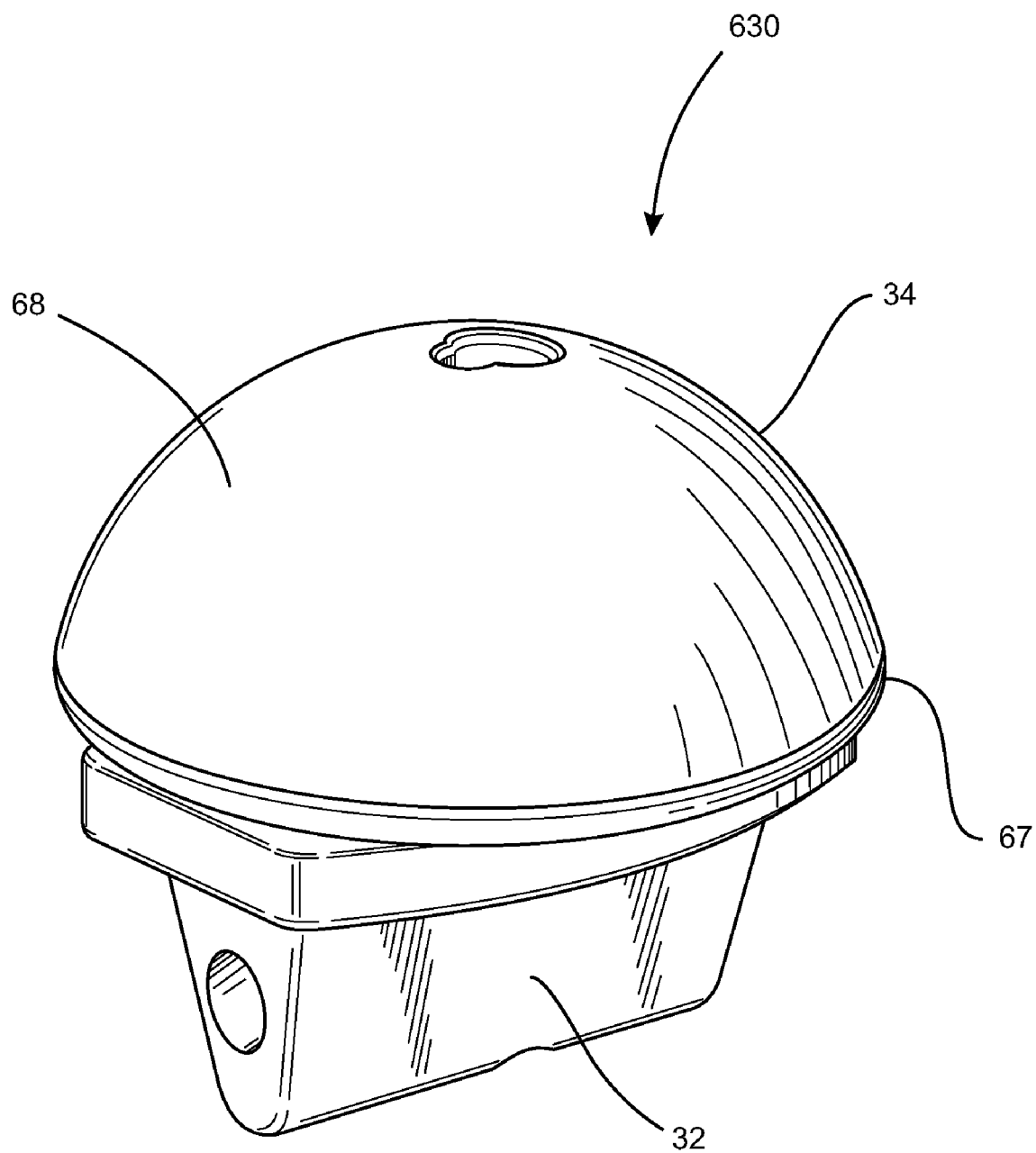
FIG. 16 is a perspective view of an alternative embodiment of a shoulder prosthesis assembly of the present disclosure.

Turning now to FIG. 16, there is shown another embodiment of a prosthesis assembly 630. The prosthesis assembly 630 is used in substantially the same manner as the prosthesis assembly 30 described herein. In addition, the prosthesis assembly 630 includes components that possess the exact same dimensions and configuration as components of the prosthesis assembly 30, with one exception. Thus, the reference numbers utilized to identify features of the prosthesis assembly 30 are utilized in FIG. 16 to identify like features of the prosthesis assembly 630.

The exception relates to the bearing 34. In particular, the bearing 34 includes a body 67 defining a bearing surface 68. The bearing surface 68 is a convex bearing surface as shown in FIG. 16 instead of a concave bearing surface as shown in FIGS. 8-10. In essentially all other aspects, the bearing 34 is constructed in the same manner as the bearing 34 of FIGS. 8-10.

Figure 17:
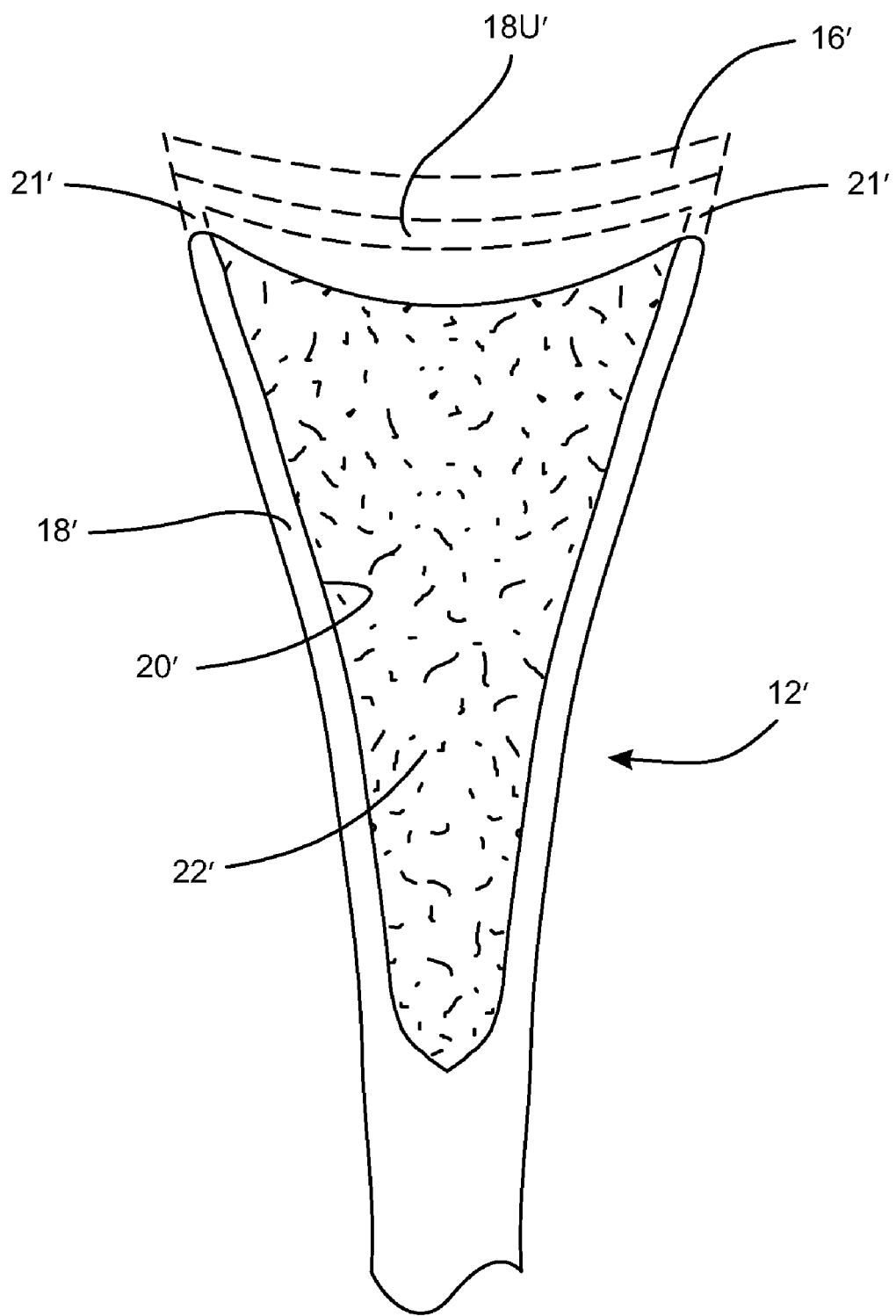
FIG. 17 is a fragmentary, inferior, cross-sectional view of a patient's scapula in which the shoulder prosthesis of FIG. 2 may be implanted, showing deterioration of the scapula in which a significant amount of subchondral and cancellous bone has been worn away.

The prosthesis assembly 30 is configured to be secured to a scapula 12' of a patient as shown in FIG. 17. Similar to the scapula 12 shown in FIG. 1, the scapula 12' shown in FIG. 17 includes subchondral bone 18' that forms walls of a glenoid vault 20' that defines a cavity which contains cancellous bone 22'. Note the scapula 12' has a significant amount of deterioration of the subchondral and cancellous bone. Indeed, a layer of cartilage 16' (shown in phantom) and an upper wall 18U' of the subchondral bone 18' including the glenoid rim 21' (both shown in phantom) no longer exist as part of the scapula 12'.

Figure 18:
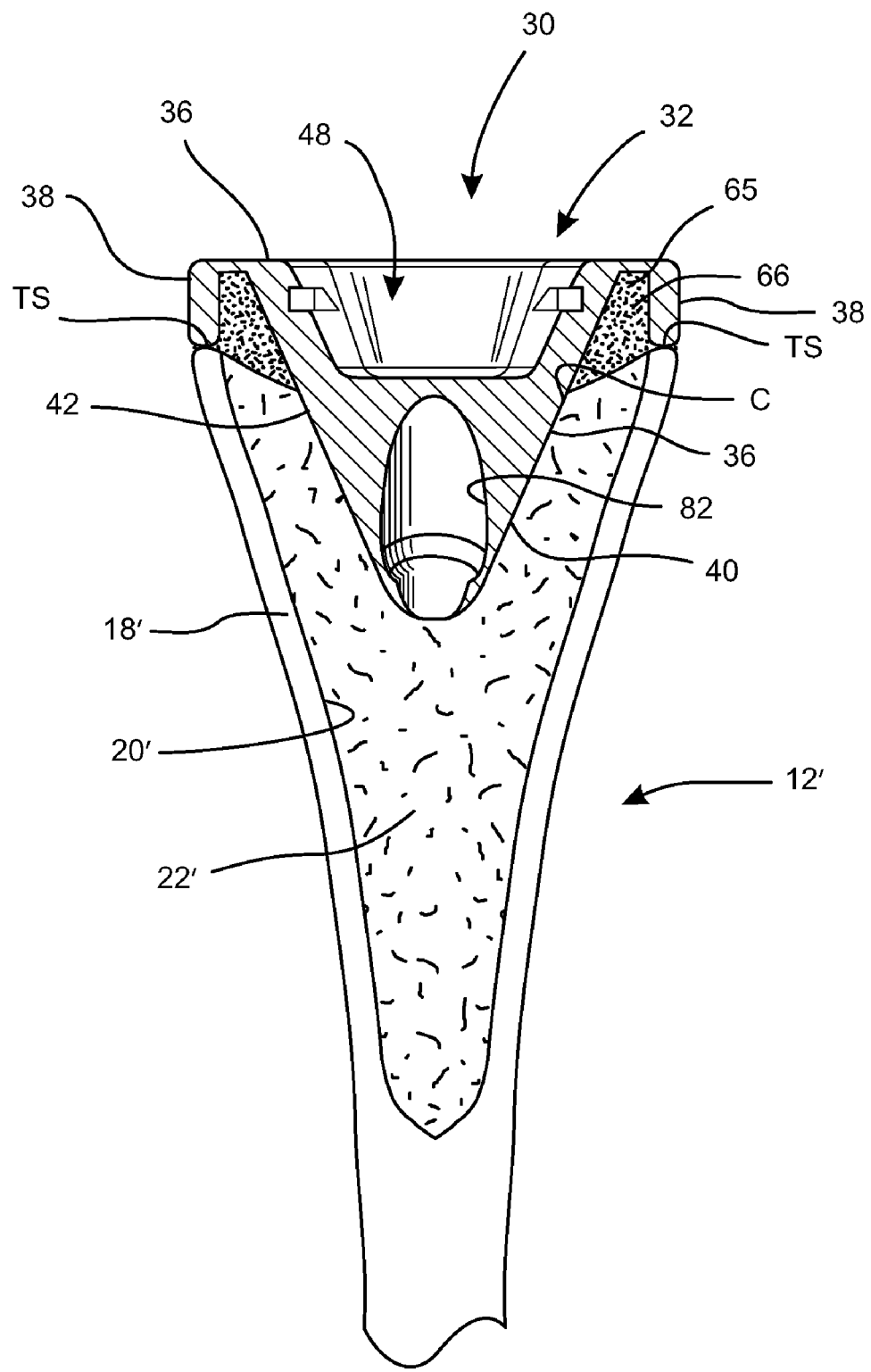
FIG. 18 is a fragmentary, inferior, cross-sectional view of the patient's scapula of FIG. 17 after implantation of the shoulder prosthesis of FIG. 2 therein, with the bearing shown removed for clarity of viewing.

FIG. 18 shows the position of the prosthesis assembly 30 after it has been implanted in the scapula 12' (note the bearing 34 is shown removed for clarity of viewing). Also note the fasteners (see, e.g., fasteners F1 and F2 of FIG. 19) are shown removed for clarity of viewing). Further note that prior to implantation of the prosthesis assembly 30 including the glenoid bearing support 32, bone of the scapula 12' is removed by surgically preparing surfaces of the glenoid vault 20' with bone shaping tools such as reamers, saws, drills, burrs, rasps, and the like. In particular, surfaces of the subchondral 18' and/or cancellous bone 22' are reshaped to form a complementary cavity C and top surface TS to receive the glenoid bearing support 32 as shown in FIG. 18.

Turning now to FIG. 19, there is shown another embodiment of a prosthesis assembly 730. The prosthesis assembly 730 is used in substantially the same manner as the prosthesis assembly 30 described herein. In addition, the prosthesis assembly 730 includes components that possess the exact same dimensions and configuration as components of the prosthesis assembly 30, with a couple exceptions. Thus, the reference numbers utilized to identify features of the prosthesis assembly 30 are utilized in FIG. 19 to identify like features of the prosthesis assembly 730.

The first exception relates to the bearing 34. In particular, the bearing 34 is a two piece bearing that includes (i) a metallic base portion 750 that couples to the glenoid bearing support 32, and (ii) a polymeric insert portion 752 that couples to the base portion 750. The insert portion 752 is configured to snap fit into the base portion 750 so as to couple the insert portion to the base portion as is well know in the art.

The second exception relates to the set of fastener channels of the glenoid vault-occupying portion 36. In particular, glenoid vault-occupying portion 36 of the prosthesis assembly 730 includes a third fastener channel 760 as shown in FIG. 19. The fastener channel 760 is configured to receive a fastener (not shown) therein in the same manner that fastener channels 82, 84 receive fasteners F1 and F2 therein, respectively. In essentially all other aspects, the prosthesis assembly 730 is constructed and operates in the same manner as the prosthesis assembly 30 shown and described herein.

There is a plurality of advantages arising from the various features of each of the embodiments of the shoulder prosthesis assembly described herein. It will be noted that alternative embodiments of the shoulder prosthesis assembly may not include all of the features described yet still benefit from at least some of the advantages of such features. Those of ordinary skill in the art may readily devise their own implementations of the shoulder prosthesis assembly that incorporates one or more of the features and fall within the spirit and scope of the present invention as defined by the appended claims.

What is claimed is:

1. A prosthesis assembly for use with a scapula, comprising:
   a glenoid bearing support including:
   a glenoid vault-occupying portion configured to occupy at least a portion of a glenoid vault of the scapula, said glenoid-vault occupying portion having a first coupling component; and
   a glenoid rim replacement portion attached to said glenoid vault-occupying portion; and
   a bearing defining a bearing surface and having a second coupling component configured to cooperate with said first coupling component to couple said bearing to said glenoid vault-occupying portion,
   wherein said glenoid vault-occupying portion defines a bearing-side end portion and an opposite-side end portion,
   wherein said glenoid rim replacement portion projects outwardly from said bearing-side end portion of said glenoid vault-occupying portion,
   wherein said glenoid bearing support defines a bone graft receptacle; and
   wherein:
      said glenoid rim replacement portion includes a plurality of vertically aligned ribs,
      said bone graft receptacle includes a plurality of sub-receptacles, and
      adjacent ribs of said plurality of vertically aligned ribs respectively form said plurality of sub-receptacles.

2. The prosthesis assembly of claim 1, wherein:
   said glenoid vault-occupying portion defines an exterior wall,
   said glenoid rim replacement portion defines an interior wall facing said exterior wall of said glenoid vault-occupying portion, and
   said exterior wall of said glenoid vault-occupying portion and said interior wall of said glenoid rim replacement portion defines said bone graft receptacle.

3. The prosthesis assembly of claim 1, wherein said glenoid rim replacement portion surrounds said bearing-side end portion of said glenoid vault-occupying portion.

4. The prosthesis assembly of claim 1, wherein said glenoid rim replacement portion surrounds said first coupling component.

5. The prosthesis assembly of claim 1, wherein said bearing surface is a concave bearing surface.

6. The prosthesis assembly of claim 1, wherein said bearing surface is a convex bearing surface.

7. The prosthesis assembly of claim 1, wherein:
said glenoid vault-occupying portion includes a first exterior wall and a second exterior wall,
when said glenoid vault-occupying portion is viewed in a cross-sectional view, said first exterior wall and said second exterior wall are positioned with respect to each other to define a generally V-shaped exterior wall,
said generally V-shaped exterior wall defines a boundary occupied in part by structure of said glenoid vault-occupying portion, and
said glenoid rim replacement portion is positioned outside of said boundary.

8. The prosthesis assembly of claim 1, wherein:
said glenoid rim replacement portion defines a bearing-facing side and a scapula-facing side,
said glenoid bearing support further defines an access opening configured to allow bone graft material to be advanced therethrough to said bone graft receptacle, and
said access opening is positioned adjacent to said scapula-facing side of said glenoid rim replacement portion.

9. The prosthesis assembly of claim 8, wherein said access opening surrounds said glenoid vault-occupying portion.

10. The prosthesis assembly of claim 1, wherein:
said glenoid vault-occupying portion includes a first exterior wall and a second exterior wall,
when said glenoid vault-occupying portion is viewed in a cross-sectional view, said first exterior wall and said second exterior wall are positioned with respect to each other to define a generally V-shaped exterior wall,
said generally V-shaped exterior wall defines a boundary occupied in part by structure of said glenoid vault-occupying portion, and
said bone graft receptacle is positioned outside of said boundary.

11. A prosthesis assembly for use with a scapula, comprising:
a glenoid bearing support including:
a glenoid vault-occupying portion configured to occupy at least a portion of a glenoid vault of the scapula, said glenoid-vault occupying portion having a first coupling component; and
a glenoid rim replacement portion attached to said glenoid vault-occupying portion; and
a bearing defining a bearing surface and having a second coupling component configured to cooperate with said first coupling component to couple said bearing to said glenoid vault-occupying portion,
wherein said glenoid vault-occupying portion defines a bearing-side end portion and an opposite-side end portion,
wherein said glenoid rim replacement portion projects outwardly from said bearing-side end portion of said glenoid vault-occupying portion,
wherein said glenoid bearing support defines a bone graft receptacle;
wherein:
said glenoid rim replacement portion includes a plurality of horizontally aligned ribs,
said bone graft receptacle includes a plurality of sub-receptacles, and
adjacent ribs of said plurality of horizontally aligned ribs respectively form said plurality of sub-receptacles.

12. A prosthesis assembly for use with a scapula, comprising:
a glenoid bearing support including:
a glenoid vault-occupying portion configured to occupy at least a portion of a glenoid vault of the scapula, said glenoid-vault occupying portion defining a coupling recess; and
a glenoid rim replacement portion attached to said glenoid vault-occupying portion and positioned to surround said coupling recess; and
a bearing defining a bearing surface and having a coupling stem which is received within said coupling recess to couple said bearing to said glenoid vault-occupying portion,
wherein said glenoid vault-occupying portion defines a bearing-side end portion and an opposite-side end portion,
wherein said glenoid bearing support defines a bone graft receptacle located adjacent to said bearing-side end portion of said glenoid vault-occupying portion, and
wherein:
said glenoid rim replacement portion includes a plurality of vertically aligned ribs,
said bone graft receptacle includes a plurality of sub-receptacles, and
adjacent ribs of said plurality of vertically aligned ribs respectively form said plurality of sub-receptacles.

13. The prosthesis assembly of claim 12, wherein:
said glenoid vault-occupying portion defines an exterior wall,
said glenoid rim replacement portion defines an interior wall facing said exterior wall of said glenoid vault-occupying portion, and
said bone graft receptacle is interposed between said exterior wall of said glenoid vault-occupying portion and said interior wall of said glenoid rim replacement portion.

14. The prosthesis assembly of claim 12, wherein said bearing surface is one of a concave bearing surface and a convex bearing surface.

15. The prosthesis assembly of claim 12, wherein:
said glenoid vault-occupying portion includes a first exterior wall and a second exterior wall,
when said glenoid vault-occupying portion is viewed in a cross-sectional view, said first exterior wall and said second exterior wall are positioned with respect to each other to define a generally V-shaped exterior wall,
said generally V-shaped exterior wall defines a boundary occupied in part by structure of said glenoid vault-occupying portion, and
said bone graft receptacle is positioned outside of said boundary.

16. A prosthesis assembly for use with a scapula, comprising:
a glenoid bearing support including:
a glenoid vault-occupying portion configured to occupy at least a portion of a glenoid vault of the scapula, said glenoid-vault occupying portion defining a coupling recess; and
a glenoid rim replacement portion attached to said glenoid vault-occupying portion and positioned to surround said coupling recess; and a bearing defining a bearing surface and having a coupling stem which is received within said coupling recess to couple said bearing to said glenoid vault-occupying portion, wherein said glenoid vault-occupying portion defines a bearing-side end portion and an opposite-side end portion, wherein said glenoid bearing support defines a bone graft receptacle located adjacent to said bearing-side end portion of said glenoid vault-occupying portion, and wherein:
said glenoid rim replacement portion includes a plurality of horizontally aligned ribs,
said bone graft receptacle includes a plurality of sub-receptacles, and
adjacent ribs of said plurality of horizontally aligned ribs respectively form said plurality of sub-receptacles.

* * * * *